US011761945B2

(12) United States Patent
Akmal et al.

(10) Patent No.: US 11,761,945 B2
(45) Date of Patent: Sep. 19, 2023

(54) WATER ANALYSIS UNIT OF A SYSTEM FOR SEPARATING AND ANALYZING A MULTIPHASE IMMISCIBLE FLUID MIXTURE AND CORRESPONDING METHOD

(71) Applicant: Saudi Arabian Oil Company, Dhahran (SA)

(72) Inventors: Naim Akmal, Dhahran (SA); Saleh Sharidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 81 days.

(21) Appl. No.: 17/482,136

(22) Filed: Sep. 22, 2021

(65) Prior Publication Data
US 2023/0090864 A1 Mar. 23, 2023

(51) Int. Cl.
*G01N 33/28* (2006.01)
*G01N 27/333* (2006.01)
(Continued)

(52) U.S. Cl.
CPC .......... *G01N 33/2847* (2013.01); *G01F 1/74* (2013.01); *G01F 25/10* (2022.01);
(Continued)

(58) Field of Classification Search
CPC .......... G01N 33/2847; G01N 27/3335; G01N 27/4167; G01N 33/2823; G01F 25/10; G01F 1/74
See application file for complete search history.

(56) References Cited

U.S. PATENT DOCUMENTS 3,712,118 A  1/1973  Mason et al.
4,481,130 A  11/1984  Robertson
(Continued)

FOREIGN PATENT DOCUMENTS

CN  101670197 B  12/2011
CN  102128658 B   7/2012
(Continued)

OTHER PUBLICATIONS

Rodriguez et al., "Treatment of Produced Water in the Permian Basin for Hydraulic Fracturing: Comparison of Different Coagulation Processes and Innovative Filter Media", MDPI Water, 12, 770, Mar. 11, 2020, pp. 1-16.
(Continued)

*Primary Examiner* — Kristina M Deherrera
*Assistant Examiner* — Jean F Morello
(74) *Attorney, Agent, or Firm* — Bracewell LLP; Constance G. Rhebergen; Keith R. Derrington

(57) ABSTRACT

A system for separating and analyzing a discrete sample of multiphase fluid includes a separation vessel having a first inner chamber containing a discrete sample of multiphase fluid, and an analytical cell in fluid communication with the separation vessel. The analytical cell has a second inner chamber containing a diluted aqueous liquid phase sample for analysis. The system further includes probes disposed in the second inner chamber, each probe having a sensing area at a distal end, and being oriented in the second inner chamber such that the sensing area is immersed in the diluted aqueous liquid phase sample contained in the second inner chamber. The plurality of probes include a first probe whose sensing area surface is coated with a first ion-exchange membrane; and a second probe whose sensing area surface is coated with a second ion-exchange mem-
(Continued)

brane, the second ion-exchange membrane being different from the first ion-exchange membrane.

21 Claims, 3 Drawing Sheets

(51) Int. Cl.
*G01F 1/74* (2006.01)
*G01F 25/10* (2022.01)
*G01N 27/416* (2006.01)

(52) U.S. Cl.
CPC ..... *G01N 27/3335* (2013.01); *G01N 27/4167* (2013.01); *G01N 33/2823* (2013.01)

(56) References Cited

U.S. PATENT DOCUMENTS

| | | | |
|---|---|---|---|
| 4,581,134 A | 4/1986 | Richter, Jr. et al. | |
| 5,078,856 A | 1/1992 | Yamaguchi et al. | |
| 5,637,201 A | 6/1997 | Raguse et al. | |
| 5,741,409 A | 4/1998 | Raguse et al. | |
| 5,753,093 A | 5/1998 | Raguse et al. | |
| 6,004,442 A * | 12/1999 | Choulga | G01N 27/3275 |
| | | | 204/415 |
| 6,872,239 B2 | 3/2005 | Nilsen et al. | |
| 7,140,441 B2 | 11/2006 | Hauge et al. | |
| 7,147,788 B2 | 12/2006 | Tveiten | |
| 7,231,819 B2 | 6/2007 | Jones et al. | |
| 7,373,813 B2 | 5/2008 | Difoggio | |
| 7,474,969 B2 | 1/2009 | Poulisse | |
| 7,661,302 B2 | 2/2010 | Gysling | |
| 7,775,085 B2 | 8/2010 | Scott | |
| 7,966,892 B1 | 6/2011 | Halilah | |
| 8,177,958 B2 | 5/2012 | Lawrence et al. | |
| 8,720,573 B2 | 5/2014 | Eriksen | |
| 8,790,509 B2 | 7/2014 | Vu | |
| 8,935,100 B2 | 1/2015 | Weiner et al. | |
| 9,052,285 B2 | 6/2015 | Muller et al. | |
| 9,239,406 B2 | 1/2016 | Kalia et al. | |
| 9,284,705 B2 | 3/2016 | Theegala | |
| 9,314,715 B2 | 4/2016 | Grave et al. | |
| 9,341,058 B2 | 5/2016 | Keizer et al. | |
| 9,540,574 B2 | 1/2017 | Janssen et al. | |
| 9,658,178 B2 | 5/2017 | Surman et al. | |
| 9,696,193 B2 | 7/2017 | Martin et al. | |
| 9,840,895 B1 | 12/2017 | Kuhn | |
| 9,863,926 B2 | 1/2018 | Kriel et al. | |
| 10,023,811 B2 | 7/2018 | Soliman et al. | |
| 10,260,010 B2 | 4/2019 | Soliman | |
| 10,350,515 B2 | 7/2019 | Al-Shafei et al. | |
| 10,597,313 B2 | 3/2020 | Raynel et al. | |
| 2012/0111571 A1 | 5/2012 | Eriksen | |
| 2013/0026082 A1 | 1/2013 | Al-Shafei et al. | |
| 2016/0052799 A1 | 2/2016 | Grave et al. | |
| 2017/0319984 A1 | 11/2017 | Oshinowo | |
| 2018/0244539 A1 | 8/2018 | Asdahl et al. | |
| 2018/0299423 A1 * | 10/2018 | Leblanc | G01N 33/2847 |
| 2019/0010796 A1 | 1/2019 | De Freitas et al. | |
| 2019/0049425 A1 | 2/2019 | Marshall et al. | |
| 2019/0211274 A1 | 7/2019 | Soliman et al. | |
| 2020/0102234 A1 | 4/2020 | Patton | |
| 2020/0255748 A1 | 8/2020 | Soliman et al. | |
| 2021/0102831 A1 | 4/2021 | Ahmad et al. | |
| 2022/0380688 A1 | 12/2022 | Soliman | |
| 2023/0086247 A1 | 3/2023 | Akmal et al. | |
| 2023/0089200 A1 | 3/2023 | Akmal et al. | |
| 2023/0093403 A1 | 3/2023 | Akmal et al. | |

FOREIGN PATENT DOCUMENTS

| | | |
|---|---|---|
| WO | 2001074468 A3 | 10/2001 |
| WO | 2021043923 A1 | 3/2021 |

OTHER PUBLICATIONS

Ghorbani et al., "Validating Automated Real-Time Produced Water Composition Measurement Device With Field Produced Water Samples: A Pathway to Filed Trial", SPE-188244-MS, Nov. 13, 2017, 2 pages.

Hach, "Complete Water Analysis for the Upstream Oil & Gas Industry", 2014, 20 pages.

Hansen et al., "Multi-Phase Flow Metering in Offshore Oil and Gas Transporlalion Pipelines: Trends and Perspectives", WWW.mdpi.com/journal/sensors, 19, 2184, May 11, 2019, pp. 1-26.

Roach et al., "A Multiphase Flow Meter for the On-Line Determination of the Flow Rates of Oil, Water and Gas", AU9817323, 1997, CSIRO Minerals, pp. 106-111.

Andreussi, P. et al.; "Application of a wet gas meter to detect extremely low liquid volume fractions" BHR Group 2007 Multiphase Production Technology 13; pp. 297-308.

* cited by examiner

WATER ANALYSIS UNIT OF A SYSTEM FOR SEPARATING AND ANALYZING A MULTIPHASE IMMISCIBLE FLUID MIXTURE AND CORRESPONDING METHOD

TECHNICAL FIELD

Embodiments of the present disclosure relate generally to a method and system for separating and analyzing multiphase immiscible fluid mixture samples. In particular, embodiments of the present disclosure relate to utilizing an improved water analysis unit equipped with ion-selective electrodes having ion-exchange membrane coated sensing areas.

BACKGROUND

Multiphase immiscible fluid mixtures (e.g., multiphase fluids) produced from oil wells typically are a mixture of gas, liquid hydrocarbons, and salty formation water (e.g., produced water). For example, an oil well may produce polar and nonpolar molecules along with gases such as carbon dioxide, hydrogen sulfide, carbon disulfide, and the like. A gas oil separation plant (GOSP) is used in the upstream oil and gas industry to refer to temporary or permanent facilities that separate the multiphase fluids obtained from a plurality of wells (e.g., more than a hundred oil wells) into constituent vapor and liquid components (e.g., liquid hydrocarbons, and salty formation or produced water) and generate dry crude oil that meets predetermined customer specifications. A typical GOSP includes a high pressure production trap (HPPT), a low pressure production trap (LPPT), a low pressure degassing tank (LPDT), a dehydrator unit, first and second stage desalting units, a water/oil separation plant (WOSEP), a stabilizer column, centrifugal pumps, heat exchangers, and reboilers.

Composition of the multiphase fluid produced from each well feeding into the GOSP typically varies over time. Generally, a greater amount of crude oil is produced initially from the well. Over time, the amount of produced water increases and the amount of crude oil produced decreases. It is necessary to know the amount of crude oil (and produced water) produced from each well of the GOSP in order to manage production of each well, while maintaining overall efficiency of the GOSP and generating dry crude that meets customer specifications. For example, if a particular well is producing a high proportion of water, it may be desirable to isolate the well from the flow of the GOSP.

A multiphase flow meter (MPFM) may be used at the GOSP (or at a well site upstream the GOSP) to measure the amount or rate of crude oil (and produced water) produced from each well. The MPFM's built-in software and algorithm can be utilized to determine the flow of oil from the combined flow of produced water and crude oil. To obtain accurate measurement of amount or flow rate of crude oil passing through the MPFM, it is necessary to calibrate the MPFM using predetermined data representing certain physical or chemical properties of the produced water contained in the multiphase fluid (including oil and water) passing through the MPFM. That is, it is necessary to enter data regarding certain properties of the produced water into the MPFM panel so that the flow meter displays information regarding the flow of oil (and flow of water) with high accuracy. To perform such calibration, conventionally, a sample of the multiphase fluid (from one well or a group of wells whose output is passing through the MPFM) is periodically collected in a test trap. The test trap can be rated as having high pressure, intermediate pressure, or low pressure. Crude oil in the sample is allowed to separate from produced water in the test trap, and a portion of the separated produced water is periodically collected and sent to a local laboratory to analyze certain geophysical or geochemical properties (e.g., salinity, chloride content, conductivity, and the like) of the separated produced water sample. The data obtained by this analysis is used to calibrate the MPFM. More specifically, the analytical result received from the laboratory is manually fed into the MPFM panel to optimize or calibrate the output of the MPFM (i.e., optimize oil flow rate data and water flow rate data coming out of the MPFM).

The periodic act of collection of the produced water sample from the test trap, transferring the sample to the laboratory, measuring the geophysical properties of the sample in the laboratory, and manually feeding the analytical data into the MPFM can take approximately two to three days. Further, since the analytical data received from the laboratory is manually fed into the MPFM, there is a possibility of introducing a human data entry error. A better approach that is faster, automated, low-maintenance, and less prone to human error is desirable.

SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the disclosed subject matter or to delineate the scope of the disclosed subject matter. Its sole purpose is to present some concepts in a simplified form as a prelude to the more detailed description that is discussed later.

In one embodiment, a water analysis unit of a system for separating and analyzing multiphase fluids is provided which includes: an analytical cell in fluid communication with a separation vessel, wherein the analytical cell has an inner chamber that is adapted to contain a diluted aqueous liquid phase sample for analysis; and a plurality of probes disposed in the inner chamber, each of the plurality of probes having a sensing area at a distal end, and being oriented in the inner chamber such that the sensing area is immersed in the diluted aqueous liquid phase sample when the diluted aqueous liquid phase sample is contained in the inner chamber, the plurality of probes including: a first probe whose sensing area surface is coated with a first ion-exchange membrane; and a second probe whose sensing area surface is coated with a second ion-exchange membrane, the second ion-exchange membrane being different from the first ion-exchange membrane.

In another embodiment, each of the first and second ion-exchange membranes is made of a sulfonated tetrafluoroethylene based fluoropolymer-copolymer, each of the plurality of probes has an oblong shape, and wherein the sensing area at the distal end of the probe is fully covered with the first or second ion-exchange membrane, and a thickness of the first or second ion-exchange membrane is between 0.003 inches and 0.01 inches.

In yet another embodiment, the first ion-exchange membrane is a perfluorinated membrane having hydrophilic properties, and the second ion-exchange membrane is an instance of the first ion-exchange membrane that has been modified by subjecting it to a predetermined treatment, and the predetermined treatment includes a boiling treatment of boiling the instance of the first ion-exchange membrane with phosphoric acid to modify a molecular structure of a polar material of the instance of the first ion-exchange membrane. In yet another embodiment, the first probe includes a first ion-selective electrode that is configured to measure a sodium or chloride concentration of the diluted aqueous liquid phase sample, and the second probe includes a second ion-selective electrode that is configured to measure one or more properties of the diluted aqueous liquid phase sample, the one or more properties selected from a group including: a total dissolved solids (TDS), pH, conductivity, sulfate concentration, carbonate concentration, and nitrate concentration. In yet another embodiment, the plurality of probes further comprise a third probe that includes a third ion-selective electrode configured to measure another one or more properties of the diluted aqueous liquid phase sample, the other one or more properties selected from the group including: TDS, pH, conductivity, sulfate concentration, carbonate concentration, and nitrate concentration.

In yet another embodiment, the plurality of probes are proximally disposed adjacent to each other such that each probe is oriented in the inner chamber in a fixed position with the sensing area in a downward direction and such that there exists an acute angle measured from the probe to a horizontal plane that is substantially perpendicular to a direction of gravity, where the acute angle is in the range of 30°-60°. In yet another embodiment, the analytical cell has a conical shape where a first width of the inner chamber on a side of a sample inlet of the analytical cell is greater than a second width of the inner chamber on a side of a sample outlet of the analytical cell, where the inner chamber of the analytical cell defines a space having a shape that funnels liquid toward the sample outlet.

In yet another embodiment, the separation vessel is external to the water analysis unit, wherein the analytical cell is in further fluid communication with an external fresh water reservoir, and the diluted aqueous liquid phase sample adapted to be contained in the analytical cell includes an aqueous liquid phase sample from the external separation vessel and a measured amount of fresh water from the external fresh water reservoir. In yet another embodiment, the water analysis unit further includes one or more processors operatively coupled to the plurality of probes, the one or more processors configured to: obtain a set of measurement data from the plurality of probes as diluted aqueous liquid phase sample data; calculate nondiluted aqueous liquid phase sample data corresponding to the aqueous liquid phase sample from the external separation vessel, based on the diluted aqueous liquid phase sample data and based on the measured amount of fresh water in the diluted aqueous liquid phase sample; and transmit the nondiluted aqueous liquid phase sample data to an external multiphase flow meter.

In yet another embodiment, a method for analyzing a diluted aqueous liquid phase sample is provided which includes the steps of: introducing a diluted aqueous liquid phase sample into an analytical cell, the diluted aqueous liquid phase sample including an aqueous liquid phase sample separated from a multiphase fluid in a separation vessel, and a measured amount of fresh water from a fresh water reservoir; analyzing the diluted aqueous liquid phase sample contained in the analytical cell with a plurality of probes disposed in an inner chamber of the analytical cell, each of the plurality of probes having a sensing area at a distal end, and being oriented in the inner chamber such that the sensing area is immersed in the diluted aqueous liquid phase sample contained in the analytical cell, wherein the plurality of probes include: a first probe whose sensing area surface is coated with a first ion-exchange membrane, and a second probe whose sensing area surface is coated with a second ion-exchange membrane, the second ion-exchange membrane being different from the first ion-exchange membrane; obtaining a set of measurement data from the plurality of probes based on the analysis as diluted aqueous liquid phase sample data; calculating nondiluted aqueous liquid phase sample data corresponding to the aqueous liquid phase sample separated from the multiphase fluid in the separation vessel, based on the diluted aqueous liquid phase sample data and based on the measured amount of fresh water in the diluted aqueous liquid phase sample; and transmitting the nondiluted aqueous liquid phase sample data to an external multiphase flow meter.

In yet another embodiment, the first ion-exchange membrane is a perfluorinated membrane having hydrophilic properties, and wherein the second ion-exchange membrane is an instance of the first ion-exchange membrane that has been modified by subjecting it to a predetermined treatment, and the predetermined treatment includes a boiling treatment of boiling the instance of the first ion-exchange membrane with phosphoric acid to modify a molecular structure of a polar material of the instance of the first ion-exchange membrane. In yet another embodiment, the first probe includes a first ion-selective electrode that is configured to measure a sodium or chloride concentration of the diluted aqueous liquid phase sample, and the second probe includes a second ion-selective electrode that is configured to measure one or more properties of the diluted aqueous liquid phase sample, the one or more properties selected from a group including: a total dissolved solids (TDS), pH, conductivity, sulfate concentration, carbonate concentration, and nitrate concentration.

In yet another embodiment, a system for separating and analyzing a discrete sample of multiphase fluid is provided which includes: a separation vessel having a first inner chamber adapted to contain a discrete sample of multiphase fluid; an analytical cell in fluid communication with the separation vessel, wherein the analytical cell has a second inner chamber is adapted to contain a diluted aqueous liquid phase sample for analysis; and a plurality of probes disposed in the second inner chamber, each of the plurality of probes having a sensing area at a distal end, and being oriented in the second inner chamber such that the sensing area is immersed in the diluted aqueous liquid phase sample when the diluted aqueous liquid phase sample is contained in the second inner chamber, the plurality of probes including: a first probe whose sensing area surface is coated with a first ion-exchange membrane; and a second probe whose sensing area surface is coated with a second ion-exchange membrane, the second ion-exchange membrane being different from the first ion-exchange membrane.

In yet another embodiment, the first ion-exchange membrane is a perfluorinated membrane having hydrophilic properties, and wherein the second ion-exchange membrane is an instance of the first ion-exchange membrane that has been modified by subjecting it to a predetermined treatment, and the predetermined treatment includes a boiling treatment of boiling the instance of the first ion-exchange membrane with phosphoric acid to modify a molecular structure of a polar material of the instance of the first ion-exchange membrane. In yet another embodiment, the first probe includes a first ion-selective electrode that is configured to measure a sodium or chloride concentration of the diluted aqueous liquid phase sample, and the second probe includes a second ion-selective electrode that is configured to measure a total dissolved solids concentration of the diluted aqueous liquid phase sample, and the plurality of probes further comprise a third probe that includes a third ion-selective electrode configured to measure a conductivity of the diluted aqueous liquid phase sample.

In yet another embodiment, the system further includes one or more processors operatively coupled to the plurality of probes, the one or more processors being configured to: introduce the discrete sample of multiphase fluid into the separation vessel via a multiphase fluid inlet of the separation vessel; mix a predetermined amount and type of demulsifier obtained from a demulsifier source with the discrete sample of multiphase fluid in the separation vessel to cause the discrete sample to separate into liquid phases including an aqueous liquid phase and a nonpolar liquid phase; draw from the separation vessel, a sample of the aqueous liquid phase in response to determining that the discrete sample has separated into the liquid phases including the aqueous liquid phase and the nonpolar liquid phase; dilute the aqueous liquid phase sample drawn from the separation vessel with a predetermined amount of fresh water from a fresh water source to generate the diluted aqueous liquid phase sample; introduce the diluted aqueous liquid phase sample into the analytical cell for analysis; measure diluted aqueous liquid phase sample data by analyzing the diluted aqueous liquid phase sample with the plurality of probes disposed in the second inner chamber; calculate the aqueous liquid phase sample data corresponding to the aqueous liquid phase sample based on the measured diluted aqueous liquid phase sample data and based on the predetermined amount of fresh water in the diluted aqueous liquid phase sample; and transmit the aqueous liquid phase sample data to an multiphase flow meter for calibration.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

Figure 1:
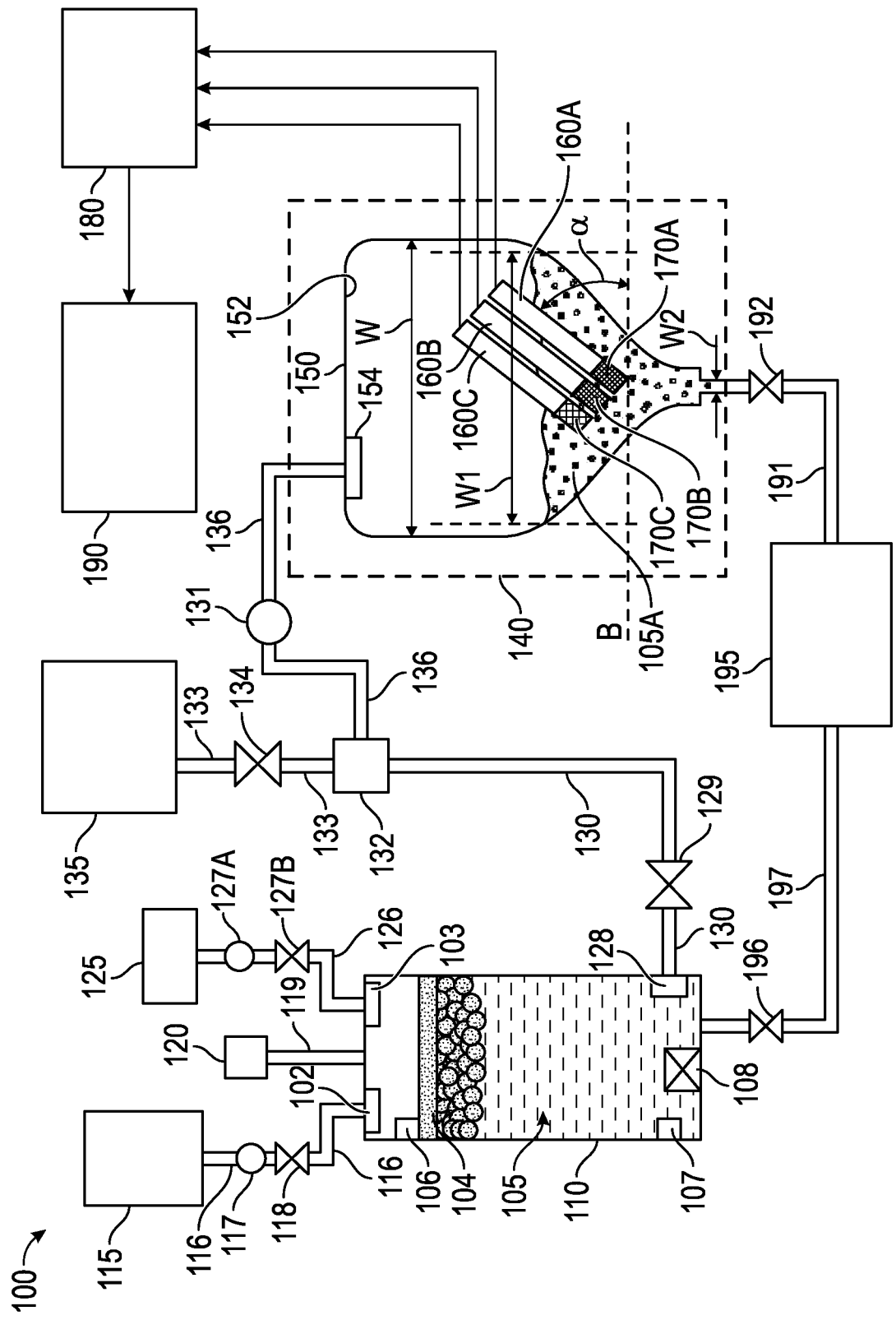
FIG. 1 is a schematic illustration of a system for separating and analyzing an aqueous liquid phase sample separated from a discrete sample of multiphase fluid, in accordance with one or more embodiments.

While certain embodiments will be described in connection with the illustrative embodiments shown herein, the subject matter of the present disclosure is not limited to those embodiments. On the contrary, all alternatives, modifications, and equivalents are included within the spirit and scope of the disclosed subject matter as defined by the claims. In the drawings, which are not to scale, the same reference numerals are used throughout the description and in the drawing figures for components and elements having the same structure.

DETAILED DESCRIPTION

In the following description, for purposes of explanation, numerous specific details are set forth in order to provide a thorough understanding of the inventive concept. In the interest of clarity, not all features of an actual implementation are described. Moreover, the language used in this disclosure has been principally selected for readability and instructional purposes, and may not have been selected to delineate or circumscribe the inventive subject matter, resort to the claims being necessary to determine such inventive subject matter. Reference in this disclosure to "one embodiment" or to "an embodiment" or "another embodiment" means that a particular feature, structure, or characteristic described in connection with the embodiment is included in at least one embodiment of the disclosed subject matter, and multiple references to "one embodiment" or "an embodiment" or "another embodiment" should not be understood as necessarily all referring to the same embodiment.

This disclosure pertains to an improved water analysis unit of a system for separating and analyzing an aqueous liquid phase sample (e.g., produced water) separated from a discrete sample of multiphase fluid (e.g., oil-water mixture) and corresponding method. The separated produced water is analyzed in the improved water analysis unit to measure properties (e.g., geophysical properties, geochemical properties, and the like) of the separated produced water sample. For example, the measured properties include pH, conductivity, salinity, chloride content, sodium content, total dissolved solids (TDS), and other ions. The water analysis unit includes an analytical cell where multiple (e.g., three or more) ion-selective electrodes (e.g., sensors, probes, and the like) are disposed (installed) in series to measure the various properties of the produced water sample. For example, the ion-selective electrodes disposed in series in the analytical cell include a first electrode to measure sodium concentration (for salinity), a second electrode to measure conductivity, and a third electrode to measure TDS, and the system is configured to automatically and simultaneously operate the three electrodes, so that the combination of the three electrodes works together to measure predetermined properties of produced water sample contained in the analytical cell to immerse the ion-selective electrodes therein.

Trace amounts of oil may remain present in the produced water sample even after the separation process of separating the produced water from the multiphase fluid. And since the ion-selective electrodes work based on electrochemical principles, when the produced water sample with even the trace amounts of oil is introduced into the analytical cell so that the ion-selective electrodes are immersed in the produced water sample to measure properties thereof, the ion-selective electrodes become easily fouled within a short period of time thereby causing measurements of the properties of the produced water sample to become inaccurate. That is, the slow buildup of oil at or near surfaces of sensing areas (e.g., sensing sections) of the ion-selective electrodes make them unresponsive to subtle changes in the intended measurement of the geophysical or geochemical properties. As a result, frequent and cumbersome manual cleaning of sensing areas of the ion-selective electrodes becomes necessary.

In order overcome the above problem, the surface of the sensing area of each ion-selective electrode according to the present disclosure is coated with a thin layer of an ion-exchange membrane. The ion-exchange membrane prevents accumulation of residual oil present in the produced water sample on the electrode, thereby preventing fouling of the ion-selective electrodes. Coating the sensing area surface with the ion-exchange membrane (or modified ion-exchange membrane, as described later) thus ensures that normal operation of the ion-selective electrodes of the water analysis unit is maintained for long periods of time, without requiring maintenance or cleaning.

The ion-exchange membrane may be a perfluorinated membrane having hydrophilic properties, and may be made of a polar material. For example, the polar material may be a sulfonated tetrafluoroethylene based fluoropolymer-copolymer. In one embodiment, the ion-exchange membrane used for coating a sensing area surface of at least a first one of a plurality of ion-selective electrodes disposed in series in the analytical cell may be an ion-exchange membrane that has been subject to a predetermined treatment (e.g., modified ion-exchange membrane; second ion-exchange membrane). The predetermined treatment may be a boiling treatment of boiling the ion-exchange membrane with pure phosphoric acid to modify the molecular structure or arrangement of the polar material of the ion-exchange membrane, thereby enhancing physical properties of the ion-exchange membrane that lead to reduced fouling even in presence of trace amounts of oil in the produced water sample being analyzed. Alternatively, the ion-exchange membrane may be boiled with other acids similar to phosphoric acid such as oligophosphoric acid or polyphosphoric acid, which are capable of improving ion-exchange properties of the membrane. The first one of the plurality of electrodes whose sensing area surface is coated with the modified ion-exchange membrane may be a TDS ion-selective electrode, conductivity ion-selective electrode, and the like. Further, the ion-exchange membrane used for coating a sensing area surface of at least a second one of the plurality of ion-selective electrodes disposed in series in the analytical cell may be an ion-exchange membrane that has not been subject to the predetermined treatment (e.g., unmodified ion-exchange membrane, first ion-exchange membrane) to enable unhindered ion-exchange and measurement. The second one of the plurality of electrodes whose sensing area surface is coated with the unmodified ion-exchange membrane may be a sodium ion-selective electrode. Protecting and coating the sensing area surfaces of the multiple ion-selective electrodes with the (modified or unmodified) ion-exchange membrane prevents fouling of the sensing areas and allows for continued operation, even in the presence of a small quantity of oil, thereby reducing the need for frequent manual cleaning of the sensing surface.

Having an accurate view of the hydrocarbons produced from a well (at a GOSP or well site) enables operators to make better decisions regarding the economic potential of the well, and of the oil field more generally. Advantageously, the method and system with improved water analysis unit disclosed here are capable of providing near-instantaneous, real-time water sample measurements for multiphase fluid samples obtained from a well that, when utilized to control, optimize or calibrate a MPFM, enables production engineers to obtain an accurate view regarding the hydrocarbon production of the well. For example, a well producing a significant water cut can be identified, and isolated if necessary, so that resources are conserved. Because the system and method disclosed herein can be automated, measurements can be carried out routinely in an unattended and uninterrupted manner with minimal labor costs and reduced potential for error. More specifically, data obtained using the system and method disclosed here can be used to calibrate, optimize, or control the MPFM, so that accurate flow rates of each phase of the multiphase fluid flowing out of the well can be measured over time. The measured data may also be used to assess the remaining productivity of the producing well. The system and method disclosed here thus enable real-time, faster, and more accurate measurement of data that provides the information necessary for the control and optimization of the oil field or of the GOSPs output.

In operation, a control unit of the system is configured to control flow of a multiphase fluid sample into a separation vessel, where liquid phases thereof are separated. The control unit may control to separate the liquid phases (e.g., oil and produced water) of the multiphase fluid sample in the separation vessel by adding a predetermined measured amount (and/or type) of demulsifier to the multiphase fluid sample in the separation vessel and operating a mixer to mix the demulsifier into the multiphase fluid sample. Still further, the control unit may be configured to cause a measured portion of the separated produced water of the multiphase fluid sample from the separation vessel to be diluted with a measured amount of fresh water and flow the diluted sample to the improved water analysis unit, where geophysical or geochemical properties of the diluted water sample are measured using the multiple sensors or probes (e.g., ion-selective electrodes). The control unit may further be configured to transmit data representing the measured properties of the separated produced water sample to an already existing MPFM associated with one or more wells from which the multiphase fluid sample was obtained to calibrate, control, or optimize the flow rate measurements for each phase by the MPFM. The MPFM may thus continuously, quickly and automatically be calibrated using multiphase fluid samples obtained in real-time to continuously and accurately calculate the flow rate of oil flowing from the GOSP (or oil field) at any given time.

The system and method of the present disclosure is thus capable of automatically monitoring geophysical or geochemical properties of produced water by taking continuous readings of multiphase fluid samples from one or more wells at the GOSP or oil field. The system can easily take samples and then measure the properties of the separated produced water for each sample and feed the measurement directly into the MPFM. The real-time water analysis unit can be installed proximal to the MPFM, and the control unit can automatically divert samples from the well to the water analysis unit to analyze geochemical properties thereof, and the control unit can further automatically transmit the measurement data for each sample from the water analysis unit to the MPFM. With the ion-selective membrane coating of the sensing area surfaces of the ion-selective electrodes in the water analysis unit, the measurements can be taken for multiple samples repeatedly and continuously with high accuracy for long periods of time without having to stop the measurement operations to clean the sensing area surfaces of the ion-selective electrodes, even when trace amounts of residual oil is present in the samples. Since the measurement data is automatically fed to the MPFM, manual sample collection and manual data entry into the MPFM is not required, and real-time measurement and monitoring for one or more wells at the GOSP or at the oil field can be automatically performed without requiring constant human supervision or interruption.

FIG. 1 is a schematic illustration of system 100 for separating and analyzing an aqueous liquid phase sample separated from a discrete sample of multiphase fluid, in accordance with one or more embodiments. System 100 represents the flow pattern and fill-up scheme of a multiphase fluid in a separation vessel, its separation, and real-time measurement of geophysical or geochemical properties of an aqueous liquid phase (e.g., produced water) separated from the multiphase fluid in improved water analysis unit 140. As shown in FIG. 1, system 100 includes separation vessel (e.g., separation chamber) 110 having an inner chamber. Separation vessel 110 may be manufactured from an at least partially translucent or transparent material such that the level of liquid inside vessel 110 can be determined by observation from outside separation vessel 110. For example, separation vessel 110 can be made of shatter-proof glass and can include markings for measuring the volume of liquid contained within. Separation vessel 110 may be configured to receive and contain a multiphase fluid from a selected well or group of wells associated with system 100. The well(s) may belong to an oil field that is serviced by a GOSP to separate the multiphase fluid produced from the well(s) into constituent vapor and liquid components, and generate dry crude oil. As shown in FIG. 1, system 100 further includes control unit 180 (e.g., programmable logic controller (PLC), central processing unit (CPU), graphics processing unit (GPU), system on a chip, application specific integrated circuit (ASIC), and the like) that may include predetermined control logic (implemented in hardware and/or software) including predetermined data and control logic to control and operate the various electronic components of system 100 shown in FIG. 1 to automate operations thereof. Although not specifically shown in FIG. 1, control unit 180 is communicatively coupled to the various electronic components of system 100 shown in FIG. 1 to communicate data and/or control signals with the components. Control unit 180 may be implemented on a computer system that is the same as or similar to computer system 300 described with regard to at least FIG. 3.

As shown in FIG. 1, separation vessel 110 has multiphase fluid inlet 102 in fluid communication with holding chamber 115 (e.g., holding tank, high-pressure fluid line, and the like) via multiphase fluid coupling 116 to receive a discrete sample of multiphase fluid based on control operation of control unit 180. Holding chamber 115 may be a high pressure, intermediate pressure or low pressure test trap for the multiphase fluid from a selected source (e.g., from a well or group of wells). Alternately, in case system 100 is implemented at a GOSP, holding chamber 115 may correspond to a high-pressure sample line where the multiphase liquid from the selected source may be flowing at a high pressure.

Pump assembly 117 and inlet control valve 118 may be disposed or installed on multiphase fluid coupling 116 to selectively start, stop, and control a flow rate of a stream of the multiphase fluid flowing through multiphase fluid coupling 116, based on control operations of control unit 180. Pump assembly 117 may be driven by one or more electric motors. Examples of electric motors used to drive pump assembly 117 include induction motors and/or permanent magnet motors. System 100 may further include one or more drives (e.g., variable frequency drives (VFDs); not shown) that monitor and control the electric motors, under control of control unit 180. The control drives, inlet control valve 118, and control unit 180 may together define a control system for automatically and selectively controlling (e.g., starting, stopping, changing flow rate, and the like) a flow of a measured amount of the multiphase fluid into separation vessel 110.

Further, as shown in FIG. 1, separation vessel 110 may be equipped with first level indicator 106 (e.g., level sensor) and second level indicator 107 (e.g., level sensor). First and second level indicators 106 and 107 may be configured to detect a liquid level or fill level inside the inner chamber of separation vessel 110. For example, second level indicator 107 may detect when the corresponding separation vessel 110 is empty (e.g., no multiphase fluid in vessel), and first level indicator 106 may detect when separation vessel 110 is full (e.g., vessel full to capacity with the discrete sample of multiphase fluid). Additional level indicators (not shown) may be installed in separation chamber 110 to detect intermediate fill levels (e.g., between full and empty) of vessel 110.

Control unit 180 may be configured to control operations of pump assembly 117 and/or control valve 118 based on sensor data indicating the fill level of separation vessel 110 received from first and second level indicators 106 and 107. For example, in response to receiving sensor data from first level indicator 106 indicating that the inner chamber of separation vessel 110 is full with the discrete sample (e.g., measured amount) of multiphase fluid, control unit 180 may be configured to control operations of pump assembly 117 and/or control valve 118 to stop flow of the multiphase fluid from holding chamber 115 into separation vessel 110 via multiphase fluid coupling 116. Similarly, in response to receiving sensor data from second level indicator 107 indicating that the inner chamber of corresponding separation vessel 110 is empty, control unit 180 may be configured to control operations of pump assembly 117 and/or control valve 118 to start flow of the multiphase fluid from holding chamber 115 into separation vessel 110 via multiphase fluid coupling 116 to fill the inner chamber of separation vessel 110 with a discrete sample of the multiphase fluid that needs to be analyzed by water analysis unit 140. First and second level indicators 106 and 107 can be devices suitable for indicating the level of liquid held in the inner chamber of separation vessel 110, such as sensors, a window, a float, and the like. Although FIG. 1 shows two level indicators 106 and 107, a person of ordinary skill will appreciate that some embodiments can use a single level indicator, and others may use more than two level indicators.

The multiphase fluid, delivered via multiphase fluid coupling 116 to separation vessel 110, can be generally characterized as a fluid that includes a mixture of at least an aqueous liquid phase (e.g., produced water) and a nonpolar liquid phase (e.g., crude oil). Analyzing the discrete sample contained in separation vessel 110 allows greater control over the separation of aqueous liquid and nonpolar liquid phases than could be achieved using a continuous process. In some embodiments, the multiphase fluid can include aqueous liquid droplets dispersed in the nonpolar liquid phase, nonpolar liquid droplets dispersed in the aqueous liquid phase, or both. The multiphase fluid can include an emulsion of aqueous liquid droplets emulsified in the nonpolar liquid phase, nonpolar liquid phase droplets emulsified in the aqueous liquid phase, or both. The aqueous liquid phase can include produced water from a corresponding well or group of wells. The nonpolar liquid phase can include crude oil produced from a corresponding well or group of wells. The multiphase fluid can contain between about 5 and 95 vol % nonpolar liquid phase and between about 5 and 95 vol % aqueous liquid phase. If the multiphase fluid contains less than about 5 vol % aqueous liquid phase there may not be a sufficient amount of water in the discrete sample received and contained in separation vessel 110 to separate it out and carry out analysis of geophysical properties thereof in water analysis unit 140. According to at least one embodiment, the multiphase fluid can have a volume ratio of nonpolar liquid phase to aqueous liquid phase that is between about 99:1 and 30:70, alternately between about 95:5 and 40:60. In one or more embodiments, the multiphase fluid includes a gas phase. The gas phase can include gases produced from a corresponding well or group of wells, such as hydrocarbons, carbon oxides, hydrogen sulfide, mercaptans, and the like. The gas phase can be dissolved in the liquid phases of the multiphase fluid when it is introduced to separation vessel 110.

As explained previously, the multiphase fluid in separation vessel 110 can be a fluid obtained from a well or a group of wells. Alternately, the multiphase fluid in separation vessel 110 may be a multiphase fluid that has at least partially been treated upstream for separation of one or more of oil, water, and gas, after the extraction of the multiphase fluid from a well or a group of wells. For example, the multiphase fluid may be a multiphase fluid that has been processed at an upstream stage (upstream to separation vessel 110) to remove dissolved gases. As the inner chamber of separation vessel 110 is filled with the multiphase fluid, gases displaced by the multiphase fluid exit separation vessel 110 via gas flow line 119. Gas flow line 119 can also be used to vent gases that come out of the multiphase fluid during or after filling separation vessel 110 and during the separation operation of the various liquid phases from the multiphase fluid filled in the inner chamber. Gas flow meter 120 may be disposed on gas flow line 119 to measure the displaced or vented gas as it exits separation vessel 110. In some embodiments, control unit 180 may be communicatively coupled to flow meter 120 to obtain a measurement of gas exiting separation vessel.

As shown in FIG. 1, system 100 further includes demulsifier source 125 that may include one or more containers or vessels (e.g., reservoirs, tanks, tubes, injectors, and the like) suitable for storing one or more types of demulsifiers. Separation vessel 110 has demulsifier inlet 103 and demulsifier source 125 may be fluidly coupled to demulsifier inlet 103 via demulsifier coupling 126 to supply a measured (known or determined) amount and a determined type of demulsifier from demulsifier source 125 to separation vessel 110, based on the characteristics of the multiphase fluid contained in separation vessel 110, under control of control unit 180. For example, control unit 180 may be configured to determine, based on known characteristics of the discrete sample of the multiphase fluid in separation vessel 110, the appropriate amount and type of demulsifier (from among a plurality of types of demulsifiers stored in source 125) to be used for introduction into separation vessel 110 and mixed with the multiphase fluid therein, so that an optimal or adequate level of separation between liquid phases including the aqueous liquid phase and the nonpolar liquid phase of the multiphase fluid in separation vessel 110 can be achieved.

Pump assembly 127A, demulsifier control valve 127B, and additional sensors (e.g., flow meters; not shown) may be disposed on demulsifier coupling 126 to introduce the measured amount and the predetermined type of demulsifier from demulsifier source 125 into separation vessel 110, under control of control unit 180. Pump assembly 127A may be driven by one or more electric motors. System 100 may further include one or more drives (e.g., VFDs; not shown) that monitor and control the electric motors under control of control unit 180. The control drives of pump assembly 127A, demulsifier control valve 127B, flow sensors (not shown), and control unit 180 may together define a control system for automatically introducing a measured amount and predetermined type of demulsifier from source 125 into separation vessel 110 based on characteristics of the discrete sample of the multiphase fluid contained therein.

The introduced measured amount and type of demulsifier from source 125 may be mixed with the multiphase fluid in separation vessel 110 to obtain a demulsified multiphase fluid. In some embodiments, control unit 180 may be configured to mix the selected amount and type of demulsifier with the multiphase fluid before the mixture is introduced into separation vessel 110. In some embodiments, control unit 180 may actively mix the demulsifier with the multiphase fluid using mixer 108 disposed inside separation vessel 110. FIG. 1 shows that mixer 108 is disposed inside separation vessel 110 at a bottom surface thereof. However, this is not intended to be limiting. Any type or number of mixers may be employed at any appropriate location inside or outside separation vessel 110 so long as the desired effect of adequately mixing the demulsifier with the multiphase fluid filled in separation vessel 110 can be achieved. Control unit 180 may be configured to turn on mixer 108 for a predetermined amount of time (e.g., 5 minutes) after the demulsifier is added to the multiphase fluid in separation vessel 110 to adequately mix the demulsifier into the multiphase fluid.

The demulsifier can be any component, such as a surface-active agent, that facilitates the aggregation of dispersed droplets of the aqueous liquid phase or the nonpolar liquid phase. Control unit 180 may be configured to automatically select the type (and amount) of demulsifier based on the type of crude oil and the amount of produced water that is typically produced from the multiphase fluid inside separation vessel 110 where the demulsifier is to be added. Nonlimiting examples of suitable demulsifiers include: polyol block copolymers, alkoxylated alkyl phenol formaldehyde resins, epoxy resin alkoxylates, amine-initiated polyol block copolymers, modified silicone polyethers, silicone polyethers, or similar components, and combinations of the same. Such demulsifiers are available from The Dow Chemical Company, Inc. and Ecolab, Inc. The amount and/or type of demulsifier that control unit 180 is configured to use can be an amount and/or type sufficient to facilitate the aggregation of dispersed droplets of the aqueous liquid phase or nonpolar liquid phase such that the bulk aqueous liquid phase and nonpolar liquid phase are separated. However, excess demulsifier can slow separation of the multiphase fluid and produce very stable emulsions. According to at least one embodiment, the amount of demulsifier control unit 180 is configured to use can be enough to produce a concentration of between about 1 and 100 ppmv demulsifier, alternately between about 1 and 50 ppmv, alternately between about 1 and 25 ppmv, alternately between about 5 and 10 ppmv.

After adding the demulsifier into the multiphase fluid in separation vessel 110 and mixing the demulsified multiphase fluid with mixer 108, control unit 180 is configured to allow the demulsified multiphase fluid to settle inside separation vessel 110 for a predetermined period of time or until a predetermined condition of the demulsified multiphase fluid is achieved, as determined based on data from one or more sensors (not shown). For example, the period of time can be predetermined to be between 1 minute and 24 hours, preferably between about 20 minutes and 12 hours, more preferably between about 1 and 5 hours. Also, the predetermined period of time may depend on the measured amount and type of demulsifier mixed into the multiphase fluid, and/or on the characteristics of the multiphase fluid in vessel 110. As a non-limiting example, the period of time can be predetermined to be approximately 2 hours. In this case, control unit 180 may be configured so that after adding the demulsifier into the multiphase fluid in separation vessel, control unit 180 may turn on mixer 108 for a predetermined amount of time (e.g., 5 minutes), and after passage of the predetermined amount of time, control unit 180 may control to turn off mixer 108, and allow the mixed demulsified multiphase fluid in separation vessel 110 to stabilize and settle for a predetermined period of time. For example, after turning off mixer 108, control unit 180 may start a timer and may determine that the demulsified multiphase fluid has adequately separated into constituent liquid phases including a separated nonpolar liquid phase and a separated aqueous liquid phase (i.e., separation operation complete) after the predetermined period of time has elapsed (e.g., after 2 hours).

In another embodiment, separation vessel 110 may be equipped with one or more sensors (not shown) that may be configured to detect sensor data, and control unit 180 may be configured to receive the sensor data and make a determination based on the sensor data as to whether the mixed and demulsified multiphase fluid has adequately separated into constituent liquid phases including a separated nonpolar liquid phase and a separated aqueous liquid phase. FIG. 1 illustrates the separation between the nonpolar liquid phase and the aqueous liquid phase of the demulsified multiphase fluid. That is, separation vessel 110 in FIG. 1 shows that the separation operation has completed so that demulsified multiphase fluid has adequately separated into liquid phases including a separated nonpolar liquid phase 104 and a separated aqueous liquid phase 105 (e.g., countdown of the predetermined period of time has ended).

As shown in FIG. 1, separation vessel 110 further includes aqueous liquid phase outlet 128, and control unit 180 may be configured to draw a measured amount of the separate aqueous liquid phase after adequate separation thereof from the demulsified multiphase fluid as an aqueous liquid phase sample. Aqueous liquid phase outlet 128 may be located in a portion of separation vessel 110 where the aqueous liquid phase is likely to accumulate in a separated form. In many cases, the aqueous liquid phase will be denser than the nonpolar liquid phase and as a result, will settle beneath the nonpolar liquid phase (as evident from FIG. 1). Therefore, as shown in FIG. 1, aqueous liquid phase outlet 128 may be located in a lower portion of separation vessel 110. In at least one embodiment, aqueous liquid phase outlet 128 can be the opening of a tube, pipe, or conduit that is located in a portion of separation vessel 110 where the aqueous liquid phase is likely to accumulate after separating.

As shown in FIG. 1, aqueous liquid phase outlet 128 may be in fluid communication with water analysis unit 140 via aqueous liquid phase coupling 130, junction 132 (e.g., manifold), and diluted sample coupling 136. Pump assembly 131 may be disposed on diluted sample coupling 136 and sample control valve 129 may be disposed on aqueous liquid phase coupling 130 to selectively start, stop, and control a flow rate of a stream of the separate aqueous liquid phase flowing through aqueous liquid phase coupling 130, under control of control unit 180. Pump assembly 131 may be driven by an electric motor. System 100 may further include one or more drives (e.g., VFDs; not shown) that monitor and control the electric motor of pump assembly 131 under control of control unit 180. The control drives, sample control valve 129, and control unit 180 may together define a control system for automatically controlling a flow of the aqueous liquid phase sample from separation vessel 110 to water analysis unit 140.

System 100 further includes fresh water reservoir (e.g., fresh water source) 135 which stores fresh water (e.g., deionized water). Fresh water reservoir 135 includes an outlet that is in fluid communication with water analysis unit 140 via fresh water coupling 133, junction 132, and diluted sample coupling 136. As shown in FIG. 1, fresh water control valve 134 may be disposed on fresh water coupling 133 to selectively start, stop, and control a flow rate of a stream of fresh water flowing through fresh water coupling 133, under control of control unit 180. The control drives of pump assembly 131, fresh water control valve 134, and control unit 180 may together define a control system for automatically controlling a flow of a measured amount of fresh water from fresh water reservoir 135 to water analysis unit 140.

During operation, when control unit 180 determines (e.g., based on passage of the predetermined period of time, or based on sensor data) that the demulsified multiphase fluid in separation vessel 110 has adequately separated into liquid phases including the separate nonpolar liquid phase and the separate aqueous liquid phase (e.g., as shown in FIG. 1), and when control unit 180 further determines that water analysis unit 140 is ready to accept a next water sample for analysis and measurement, control unit 180 may be configured to control sample control valve 129 and pump assembly 131 to draw a predetermined measured amount of the aqueous liquid phase (e.g., aqueous liquid phase sample; nondiluted aqueous liquid phase sample) from separation vessel 110 via aqueous liquid phase coupling 130. Control unit 180 may further be configured to control fresh water control valve 134 and pump assembly 131 to draw a predetermined measured amount of fresh water from reservoir 135 via fresh water coupling 133 to cause a stream of the aqueous liquid phase sample received via aqueous liquid phase coupling 130 to mix with a stream of the predetermined amount of fresh water received via fresh water coupling 133 at junction 132, and thereby generate a diluted aqueous liquid phase sample 105A.

Control unit 180 may further be configured to convey the diluted aqueous liquid phase sample to water analysis unit 140. That is, control unit 180 may be configured to control the sample control valve 129, fresh water control valve 134, and pump assembly 131 to deliver and mix fresh water from fresh water reservoir 135 and the separated aqueous liquid phase sample from the separation vessel 110 at junction 132 to obtain the diluted aqueous liquid phase sample, and convey the diluted aqueous liquid phase sample to water analysis unit 140 via diluted sample coupling 136. Alternately, control unit 180 may be configured to control the sample control valve 129, fresh water control valve 134, and pump assembly 131, such that the separated aqueous liquid phase sample from the separation vessel 110 is conveyed to water analysis unit 140 via diluted sample coupling 136 separately from conveyance of the predetermined amount of fresh water from fresh water reservoir 135 to water analysis unit 140 via diluted sample coupling 136, so that the mixing and generation of the diluted aqueous liquid phase sample occurs (at least partially) inside water analysis unit 140.

Control unit 180 may control sample control valve 129 and pump assembly 131 to deliver the predetermined measured amount (i.e., mass, volume, or both) of the aqueous liquid phase as the aqueous liquid phase sample that is to be mixed with the fresh water prior to the measurement. For example, control unit 180 may utilize data from one or more sensors (e.g., flow meters; not shown) disposed on aqueous liquid phase coupling 130 to deliver the aqueous liquid phase sample having the measured amount. Similarly, control unit 180 may control fresh water control valve 134 and pump assembly 131 to deliver the predetermined measured amount (i.e., mass, volume, or both) of the fresh water as the predetermined amount of fresh water to dilute the aqueous liquid phase sample and generate the diluted aqueous liquid phase sample. For example, control unit 180 may utilize data from one or more sensors (e.g., flow meters; not shown)

disposed on fresh water coupling 133 to deliver the fresh water having the measured amount.

The amount of fresh water used to dilute the aqueous liquid phase sample can be predetermined based on preset criteria (e.g., type of multiphase fluid from which the aqueous liquid phase has been separated, application requirements, sensing capacity of probes in water analysis unit 140, number of probes, size of analytical cell 150 of water analysis unit 140, and the like). For example, the ratio of fresh water to aqueous liquid phase in the diluted aqueous liquid phase sample can be between about 50:1 and 1:1, preferably between about 30:1 and 1:1, more preferably between about 10:1 and 15:1. As a specific (non-limiting) example, the ratio of fresh water to aqueous liquid phase in the diluted aqueous liquid phase sample that is contained in analytical cell 150 of water analysis unit 140 is 10:1.

As shown in FIG. 1, system 100 further includes water analysis unit 140 in fluid communication with separation vessel 110 and with fresh water reservoir 135. Water analysis unit 140 is configured to receive the aqueous liquid phase sample from separation vessel 110 and receive the measured amount of fresh water from fresh water reservoir 135 under control of control unit 180. Water analysis unit 140 includes at least one analytical cell 150, and one or more probes (e.g., sensors, electrodes) 160 (e.g., 160A-160C) for measuring properties of the diluted aqueous liquid phase sample. The properties measured may include total dissolved solids (TDS), salinity, pH, conductivity, sodium concentration, chloride concentration, sulfate concentration, carbonate concentration, nitrate concentration, and the like. Each probe 160 installed in water analysis unit 140 for measuring one or more physical or chemical properties of the diluted aqueous liquid phase sample delivered to analytical cell 150 may include an ion-selective electrode. Each probe 160 may have a stainless-steel body and have a sensing area (e.g., sensing region, sensing section) at a tip of the probe that is adapted to be immersed in and come into contact with the diluted aqueous liquid phase sample contained in analytical cell 150 to measure the one or more physical or chemical properties of the diluted aqueous liquid phase sample. The each sensing area surface may be coated with an ion-exchange membrane to define a membrane-coated sensor tip (e.g., measuring tip) 170. The coating may provide ruggedness, protect the sensing area from corrosion, and prevent fouling of the sensing area.

Diluting the aqueous liquid phase sample with fresh water ensures that the capacity of each probe 160 is not overloaded and increases the volume of the relatively small aqueous liquid phase sample so that the sample can be analyzed by and adequately immerse each probe 160 disposed in series inside analytical cell 150. That is, the dilution step (e.g., diluting the produced water sample with a sample of fresh water by 10-15 times) enables application of multiple ion-selective electrodes for measurement of properties of the produced water sample in series in analytical cell 150, while also ensuring that the measured properties remain within the specified operating range of the ion-selective electrodes. This step can also reduce the corrosive potential of the aqueous liquid phase sample, allowing system 100 components to be manufactured from materials which might otherwise be unsuitable.

As shown in FIG. 1, analytical cell 150 of water analysis unit 140 defines inner chamber 152 and is in fluid communication with separation vessel 110 and fresh water reservoir 135 via diluted sample inlet 154. Inner chamber 152 defines a space having a shape that narrows toward a minimum point (e.g., a funnel shape, conical shape, rounded bottom, and the like) to provide a suitable depth of the diluted aqueous liquid phase sample contained therein so that each membrane-coated sensor tip 170 of each probe 160 disposed in analytical cell 150 can be adequately immersed in and come into contact with the diluted aqueous liquid phase sample, without requiring large volumes of the diluted aqueous liquid phase sample. In addition to improving the depth of the diluted aqueous liquid phase sample and providing a much smaller volume than an analytical cell with a flat bottom, the shape of analytical cell 150 also improves the accuracy of subsequent measurements. This is because, it has been found that subsequent diluted aqueous liquid phase samples can be contaminated by liquid that remains in analytical cell 150 after measurement and draining, if it does not have a shape that funnels liquid toward an outlet. By designing analytical cell 150 to have a shape that narrows toward a minimum point, analytical cell 150 can be more completely emptied using only the force of gravity, thereby preventing cross contamination between samples and resulting in increased accuracy of each sample measurement.

As shown in FIG. 1, analytical cell 150 may have a conical or funnel shape, where cell width W represents a maximum distance across an inner cross section of analytical cell 150 taken perpendicular to the direction of gravity. The portion of analytical cell 150 that is wetted by the diluted aqueous liquid phase sample when present inside the analytical cell may have cell width that decreases in the downward direction (i.e., the direction of gravity). For example, upper cell width W1 represents the width measured at the meniscus of the diluted aqueous liquid phase sample after analytical cell 150 has been filled, and lower cell width W2 represents the width measured at the lowest portion of analytical cell 150 that is wetted by the diluted aqueous liquid phase sample. As shown in FIG. 1, the cell width between upper cell width W1 and the lower cell width W2 decreases in the direction of gravity so that upper cell width W1 is greater than lower cell width W2. W1 and W2 may have a ratio between about 21:20 and 100:1, preferably between about 11:10 and 80:1, more preferably between about 5:4 and 50:1, even more preferably between about 3:2 and 30:1. Another advantage of analytical cell 150 having a conical shape as shown in FIG. 1 (over an analytical cell having a uniform narrow (tube-like) width is that a plurality of probes 160A-160C can be located proximally (e.g., adjacent or next to each other as shown in FIG. 1) inside analytical cell 150 instead of being spaced vertically.

In the example implementation shown in FIG. 1, three probes 160A-160C are disposed inside analytical cell 150. The number of analytical cells 150 and the number of probes 160 inside each analytical cell is not intended to be limiting. The number and type of probes 160, the number of analytical cells 150, and the relationship between the probes 160 and analytical cell 150 may be determined based on the particular application requirements. In some embodiments, each probe 160 may be disposed in a separate analytical cell 150. For example, a first probe 160 may be disposed in a first analytical cell 150, a second probe 160 may be disposed in a second analytical cell 150, and so on. Also, embodiments of water analysis unit 140 according to the present disclosure may include one or two or four or more analytical cells 150, each with a corresponding number of (one or more) probes 160. Any suitable configuration of analytical cell(s) and probe(s) inside the analytical cells can be deployed in water analysis unit 140 so long as desired geophysical or geochemical properties of the diluted aqueous liquid phase sample can be measured and recorded, and other advantages of water analysis unit 140 consistent with this disclosure can be realized.

Further, in the embodiment shown in FIG. 1, system 100 includes a single separation vessel 110. This is not intended to be limiting. Other embodiments of system 100 may include multiple separation vessels 110, each in fluid communication with water analysis unit 140 via corresponding set of components similar to those described in FIG. 1 for separation vessel 110 to automatically deliver a corresponding separated aqueous liquid phase sample for analysis and measurement. Still further, in the embodiment of FIG. 1, analytical cell 150 is disposed separately from separation vessel 110. However, in other embodiments, analytical cell 150 may be disposed inside (in-situ) separation vessel 110 so that the separated aqueous liquid phase sample contained in separation vessel can be directly delivered in-situ to analytical cell 150 inside separation vessel 110 for analysis and measurement. Also, the size, shape, and other characteristics of analytical cell 150, probes 160, and membrane-coated sensor tips 170 are not intended to be limiting to what is illustrated in FIG. 1. Any suitable size, shape, and other characteristics of analytical cell 150, probes 160, and membrane-coated sensor tips 170 may be employed so as to measure desired one or more physical or chemical properties of the diluted aqueous liquid phase sample introduced in analytical cell 150, so long as the advantages of advantages of system 100 consistent with this disclosure can be realized.

In the exemplary implementation of FIG. 1, membrane-coated sensor tips 170A-170C of the plurality of probes 160A-160C are positioned in analytical cell 150 such that they can be immersed in the diluted aqueous liquid phase sample after the sample has been introduced to analytical cell 150. Probes 160A-160C may have an oblong shape with respective membrane-coated sensor tips 170A-170C located at a distal end. Probes 160A-160C can be oriented in a fixed position with respective membrane-coated sensor tips 170A-170C in the downward direction so that there exists an acute angle $\alpha$ measured from each probe 160 to a horizontal plane B. Orienting each probe 160 in this manner has the effect of allowing each probe 160 to be positioned so that corresponding membrane-coated sensor tip 170 can be positioned and immersed in the diluted aqueous liquid phase sample having a limited volume (e.g., volume that is insufficient to completely fill analytical cell 150 as shown in FIG. 1). Also, compared with probes oriented in a vertical or horizontal direction, orienting probes 160A-160C at an acute angle has the effect of reducing the accumulation of oil droplets near membrane-coated sensor tips 170A-170C, thereby preventing fouling and requiring less frequent maintenance and cleaning. The acute angle $\alpha$ can be between about 80° and 10°, preferably between about 60° and 30°. The acute angle $\alpha$ can vary based on the conical wall defining inner chamber 152 of analytical cell 150 or based on the shape of analytical cell 150. In at least one embodiment, the acute angle $\alpha$ is 45°.

As explained previously, membrane-coated sensor tip 170 of each electrode or probe 160 corresponds to a sensing area of the electrode whose surface is coated with an ion-exchange membrane to prevent accumulation of oil at or near the sensing area. Even when present in extremely limited quantities, oil in the diluted aqueous liquid phase sample can foul the sensing area of the probes and cause inaccurate measurements. The membrane coating helps prevent the accumulation of oil droplets at or near the sensing area. The ion-exchange membrane used for coating the sensing area may be a perfluorinated membrane having hydrophilic properties and may be made of a polar material. The ion-exchange membrane may be directly applied to the sensing area surface of each electrode 160 to allow exchange of water but prevent oil droplets from sticking to the sensing area surface of each electrode 160. The sensing area surface of each probe 160 may be completely enveloped by the ion-exchange membrane so that no portion of the sensing area surface is left directly exposed to the diluted aqueous liquid phase sample when present in analytical cell 150. The polar material of the ion-exchange membrane may be any material suitable for coating the sensing area that is to be used in an aqueous environment. The polar material may be any suitable material that is sufficiently permeable to allow the diluted aqueous liquid phase sample to contact the sensing area surface of each probe 160, while blocking any residual oil from contacting the sensing area. For example, the polar material can include a polymer such as polyvinyl acetate, polyimide, polybenzimidazole, polyacrylonitrile, polyethersulfone, sulfonated tetrafluoroethylene-based fluoropolymer-copolymer, or similar materials, and combinations of the same. The polar material ion-exchange membrane coated on the sensing area may have a thickness between about 0.003 inches and 0.01 inches. In an exemplary embodiment, the ion-exchange membrane coated on the sensing area surface of each probe 160 has a thickness of approximately 183 micrometers (0.007 inches), and the polar material ion-exchange membrane is a sulfonated tetrafluoroethylene-based fluoropolymer-copolymer, available under the brand name Nafion™. Nafion™ is a trademark of The Chemours Company FC, LLC, Wilmington, Del. As a non-limiting example, the polar material ion-exchange membrane is Nafion™ 117.

In the embodiment of FIG. 1, sensing area surfaces of ion-selective electrodes 160A and 160B are coated with the perfluorinated, hydrophilic ion-exchange membrane that has been subject to a predetermined treatment to modify the structure of the polar material of the ion-exchange membrane (i.e., modified ion-exchange membrane; modified membrane-coated sensor tips 170A and 170B) and thereby enhance physical property of the membrane to prevent accumulation of oil droplets near the sensing areas of ion-selective electrodes 160A and 160B. The predetermined treatment may include a boiling treatment in which the ion-exchange membrane is boiled with pure phosphoric acid. The boiling treatment modifies the molecular structure or arrangement of the polar material of the ion-exchange membrane. The resultant modified membrane-coated sensor tips 170A and 170B have an increased operation range so that even the presence of small amounts of oil in the produced water does not hamper normal operation and accurate measurement of ion-selective electrodes 160A and 160B. During the predetermined treatment, the ion-exchange membrane may be boiled with phosphoric acid for at least ten minutes and then allowed to cool down. Any excess phosphoric acid may be removed by wiping with a clean tissue paper, until there is no more free phosphoric acid attached to the surface of the ion-exchange membrane. Then, a 5% solution of the treated ion-exchange membrane may be prepared in a mixture of isopropyl alcohol and water. A thin layer of such treated solution is applied on the surface of the sensing areas of ion-selective electrodes 160A and 160B and allowed to dry. Upon drying, a very thin coating of the treated ion-exchange membrane results on the sensing areas of ion-selective electrodes 160A and 160B.

Further, in the embodiment of FIG. 1, the sensing area of ion-selective electrode 160C disposed inside analytical vessel 150 is coated with the perfluorinated, hydrophilic ion-exchange membrane. However, the ion-exchange membrane used to coat the sensing area of ion-selective electrode 160C is not subject to the predetermined treatment, thereby coating the sensing area of ion-selective electrode 160C with the ion-exchange membrane in its original form, without any modification to the molecular structure or arrangement of the polar material of the ion-exchange membrane. Application of the ion-exchange membrane in its original form serves the purpose of accurately monitoring sodium concentration in the water sample due to presence of pendant —$SO_3Na$ group in the ion-exchange membrane. Presence of this pendant group allows for unhindered monitoring of sodium in the produced water (i.e., in the diluted aqueous liquid phase sample in analytical cell 150). Thus, the reading received from ion-selective electrode 160C can be translated to the amount of chloride ions present in the produced water sample, thereby enabling unhindered and accurate measurement of sodium in the produced water sample.

In case of ion-selective electrodes 160A and 160B, the membrane is treated (e.g., boiled) with pure phosphoric acid, allowing for replacement of pendant —$SO_3Na$ group of the ion-exchange membrane with —$SO_3H$ group (e.g., sulfonic acid). The presence of —$SO_3H$ group helps to maintain flow of electrons to preserve functionality of the electrodes. Even oil present at sub ppm levels in the produced water sample has the potential to foul the sensing surface of the electrodes over a few days of operation. By coating sensing area surfaces of electrodes 160A and 160B with the modified ion-exchange membrane, the property of preventing accumulation of oil droplets near the sensing area of the electrode is enhanced even further.

As a non-limiting example, probe 160C may be a sodium ion-selective electrode that is is used to measure sodium content, and membrane-coated sensor tip 170C includes the perfluorinated, hydrophilic ion-exchange membrane (e.g., Nafion™ 117) in its original form, probe 160A may be TDS ion-selective electrode that is being used to measure TDS content, and probe 160C may be a conductivity ion-selective electrode that is being used to measure conductivity, where modified membrane-coated sensor tips 170A and 170B of probes 160A and 160B include the perfluorinated, hydrophilic ion-exchange membrane (e.g., Nafion™ 117) that has been subjected to the predetermined treatment of boiling with phosphoric acid to modify the molecular structure or arrangement of the polar material of the ion-exchange membrane.

During operation, control unit 180 controls components of system 100 to introduce the diluted aqueous liquid phase sample in analytical cell 150 to fill analytical cell 150 (e.g., as shown in FIG. 1) with the diluted aqueous liquid phase sample such that membrane-coated sensor tips 170A-170C (e.g., modified membrane-coated sensor tip(s), unmodified membrane-coated sensor tip(s)) of probes 160A-160C are immersed in and comes in predetermined contact with the diluted aqueous liquid phase sample. Control unit 180 may further be configured to control components of system 100 so that the diluted aqueous liquid phase sample in analytical cell 150 remains in contact with respective membrane-coated sensor tips 170A-170C of probes 160A-160C during a measurement operation for a predetermined period of time. The predetermined period of time may be preset (e.g., approximately 15 minutes), or may be determined based on predetermined logic of control unit 180. For example, the predetermined logic of control unit 180 may detect when the measurement or output of probes 160A-160C has stabilized so as to determine that a steady reading from the sensor has been obtained. And control unit 180 may be configured to maintain the diluted aqueous liquid phase sample in analytical cell 150 in contact with respective membrane-coated sensor tips 170A-170C of probes 160A-160C until the steady reading has been detected and recorded. Alternately, the period of time of the measurement operation can be predetermined to be between 30 seconds and 1 hour, preferably between about 1 minute and about 20 minutes, more preferably between about 5 minutes and 15 minutes. Once control unit 180 detects the stable reading or once the predetermined period of time has elapsed, control unit 180 stores in memory, a set of measurement data corresponding to the output of probes 160A-160C as diluted aqueous liquid phase sample data. Control unit 180 may record the diluted aqueous liquid phase sample data in association with other relevant data such as data regarding the multiphase fluid from which the aqueous liquid phase sample was drawn, demulsifier data, source well information, and the like.

Control unit 180 may further be configured to calculate approximate corresponding values from the diluted aqueous liquid phase sample data for the nondiluted aqueous liquid phase sample by adjusting the diluted aqueous liquid phase sample data to account for the measured amount of dilution with fresh water. That is, control unit 180 may be configured to calculate and record in memory, a set of measurement data corresponding to the nondiluted aqueous liquid phase sample as the nondiluted aqueous liquid phase sample data (i.e., aqueous liquid phase sample data), based on the recorded set of measurement data corresponding to diluted aqueous liquid phase sample, and based on data regarding the ratio of fresh water to aqueous liquid phase in the diluted aqueous liquid phase sample. Control unit 180 can also be configured to adjust the calculated nondiluted aqueous liquid phase sample data to account for properties of the fresh water used for the dilution. For example, if the property to be approximated is the concentration of a solute, the processing unit 180 can be configured to adjust the calculated nondiluted aqueous liquid phase sample data to account for a known preexisting concentration of the solute in the fresh water that is used to dilute the aqueous liquid phase sample.

As shown in FIG. 1, system 100 may further include MPFM 190 that is communicatively coupled to control unit 180. MPFM 190 may be used to measure the flow rate of each phase of a multiphase fluid (e.g., including at least oil and produced water) of a well or a group of wells at a GOSP or at a well site. Control unit 180 may be configured to transmit the calculated values corresponding to the nondiluted aqueous liquid phase sample data (e.g., (adjusted or recorded) set of measurement data corresponding to nondiluted aqueous liquid phase sample) to MPFM 190 to calibrate, optimize, or control MPFM 190, so that MPFM 190 can detect flow rates of each phase (e.g., oil and produced water) passing therethrough more accurately.

A drain outlet of analytical cell 150 may be in fluid communication with drain equipment 195 via water analysis coupling 191. Analytical cell control valve 192 may be disposed on water analysis coupling 191 to selectively start, stop, and control a flow rate of a stream of the diluted aqueous liquid phase sample (or fresh water) being drained out of analytical cell 150 under control of control unit 180. After the diluted aqueous liquid phase sample has been analyzed by probes 160A-160C and corresponding diluted aqueous liquid phase sample data recorded, control unit 180 may control analytical cell control valve 192 to remove (drain) the diluted aqueous liquid phase sample from analytical cell 150 via water analysis coupling 191 to drain equipment 195. Although not shown in FIG. 1, system 100 may include a pump assembly to remove the diluted aqueous liquid phase sample from analytical cell 150 and flow the diluted aqueous liquid phase sample to drain equipment 195. Analytical cell control valve 192, control drives (if any) and control unit 180 may together define a control system for automatically controlling draining of the diluted aqueous liquid phase sample out of analytical cell 150. After draining the diluted aqueous liquid phase sample, control unit 180 may further be configured to control pump assembly 131 and control valve 134 to flow fresh water from fresh water reservoir 135 into analytical cell 150 to thereby flush (e.g., rinse) analytical cell 150 with fresh water and prepare the cell to receive subsequent samples without any cross contamination between the samples.

Further, as shown in FIG. 1, separation vessel 110 may be in fluid communication with drain equipment 195 via drain coupling 197 to drain the demulsified multiphase fluid in separation vessel 110, after the aqueous liquid phase sample has been extracted therefrom via aqueous liquid phase outlet 128, or after the corresponding diluted (or nondiluted) aqueous liquid phase sample data has been recorded by control unit 180 in memory. Drain control valve 196 may be disposed on drain coupling 197 to selectively start, stop, and control a flow rate of a stream of the demulsified and separated multiphase fluid being drained out of separation vessel 110 under control of control unit 180. Drain control valve 196, and control unit 180 may together define a control system for automatically controlling draining of the demulsified and separated multiphase fluid out of separation vessel 110. Thus, after the diluted aqueous liquid phase sample has been analyzed by sensors 160A-160C and corresponding diluted aqueous liquid phase sample data recorded (or after the corresponding aqueous liquid phase sample has been drawn from separation vessel 110), control unit 180 may control drain control valve 196 to drain the demulsified and separated multiphase fluid from separation vessel 110 via drain coupling 197 to drain equipment 195, and prepare emptied separation vessel 110 for a next sample of multiphase fluid. After emptying (e.g., based on second level indicator 107 indicating that the inner chamber of separation vessel 110 is empty) separation vessel 110, control unit 180 may also be configured to flush (e.g., rinse) the inner chamber of separation vessel 110 with fresh water from reservoir 135 in preparation for receiving a next discrete sample of multiphase fluid.

The above process of system 100 thus repeats with each new discrete sample of the multiphase fluid introduced into separation vessel 110 after analysis for a previous discrete sample of the multiphase fluid has been completed. The process can be automated by control unit 180 so that discrete samples of the multiphase fluid in separation vessel 110 are continuously measured in real-time, sets of measurement data recorded in memory, and the data transmitted to MPFM 190 for calibrating, optimizing, or controlling accuracy of data output from MPFM 190 with minimal or no supervision. The automation allows direct feeding of data to the MPFM to streamline and expedite the process of well monitoring, while reducing error. The system 100 can thus be used to analyze discrete multiphase fluid samples from one or more wells, allowing less-productive wells to be identified and isolated. Further, the (modified or unmodified) membrane-coated sensor tips 170A-170C ensure that the measurement operation can be repeatedly and accurately performed for multiphase fluid samples for long periods of time, without requiring frequent cleaning of the electrodes.

Figure 2:
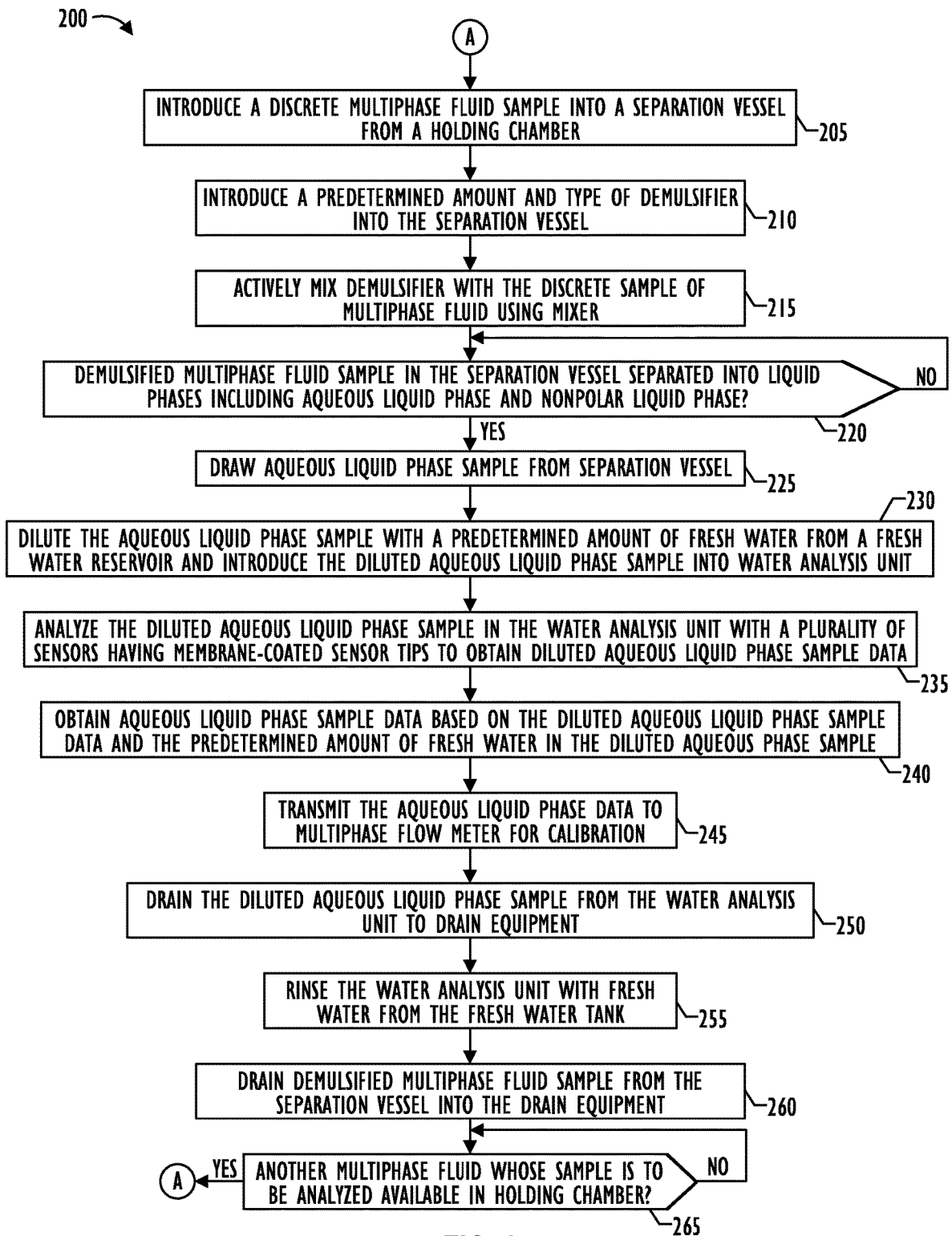
FIG. 2 is a flow chart that illustrates a method of operation of the system for separating and analyzing the aqueous liquid phase sample separated from the discrete sample of multiphase fluid, in accordance with one or more embodiments.

FIG. 2 is a flow chart that illustrates method 200 of operation of the system illustrated in FIG. 1, in accordance with one or more embodiments. Method 200 begins at block 205 where a discrete sample of multiphase fluid is introduced into separation vessel 110 from holding chamber 115. At block 205, in response to control unit 180 determining (e.g., based on data received from corresponding first and second level indicators 106 and 107) that separation vessel 110 is in an empty state, and also determining (e.g., based on sensor data) that holding chamber 115 contains multiphase fluid that needs to be analyzed, control unit 180 may control pump assembly 117 and inlet control valve 118 disposed on multiphase fluid coupling 116 of separation vessel 110 to permit a discrete sample of the multiphase fluid in holding chamber 115 to flow into and fill the separation vessel 110. For example, control unit 180 may control to continue the filling operation until level indicators 106 and 107 indicate that separation vessel 110 is in a full state. The discrete sample of multiphase fluid may be associated with a selected well or a selected group of wells whose produced water sample needs to be analyzed to measure properties thereof, and calibrate, control, or operate the MPFM based on the measurement.

Method 200 then proceeds to block 210 where control unit 180 controls pump assembly 127A and control valve 127B to introduce a predetermined measured amount and type of demulsifier from demulsifier source 125 into separation vessel 110 filled at block 205. At block 210, control unit 180 is configured to determine the measured amount and type of demulsifier to be introduced into separation vessel 110 based on predetermined data representing the type of crude oil and the amount of produced water that is typically produced from the multiphase fluid inside separation vessel 110 filled at block 205. At block 215, control unit 180 controls mixer 108 to actively mix the demulsifier with the multiphase fluid in separation vessel 110 (i.e., mixing operation). Control unit 180 may be configured to operate mixer 108 for a predetermined period of time (e.g., 5 minutes) after the demulsifier is added to the multiphase fluid in separation vessel 110 at block 210.

Method 200 then proceeds to block 220 where control unit 180 determines whether the discrete sample of multiphase fluid contained in separation vessel 110 has adequately separated into liquid phases including a separate aqueous liquid phase and a separate nonporous liquid phase. At block 220, control unit 180 may be configured to determine that adequate separation has been achieved (i.e., oil-water separation operation completed) based on passage of a predetermined period of time since completion of the active mixing operation at block 215. For example, control unit 180 may determine that adequate separation for the discrete sample in separation vessel 110 has been achieved when approximately 2 hours have elapsed since completion of the mixing operation at block 215. Alternately, or in addition, control unit 180 at block 220 may be configured to determine that adequate separation for the discrete sample has been achieved (i.e., separation operation complete) based on sensor data from one or more sensors (e.g., optical sensors, conductivity sensors, and the like) disposed in separation vessel 110 making such indication.

In response to control unit 180 determining that the discrete sample in separation vessel 110 as adequately separated into liquid phases including the separate aqueous liquid phase and the separate nonporous liquid phase (YES at block 220; separation operation completed), method 200 proceeds to block 225 where control unit 180 controls pump assembly 131 and sample control valve 129 to draw a measured amount of the separated aqueous liquid phase (i.e., aqueous liquid phase sample) from separation vessel 110 for analysis and measurement. Method 200 then proceeds to block 230 where control unit 180 controls fresh water control valve 134 and pump assembly 131 to flow and mix a measured amount of fresh water from fresh water reservoir 135 with the aqueous liquid phase sample drawn at block 225 to generate a diluted aqueous liquid phase sample, and flow the diluted aqueous liquid phase sample to analytical cell 150 of water analysis unit 140.

At blocks 225 and 230, control unit 180 may be configured draw a measured amount of the aqueous liquid phase as a nondiluted aqueous liquid phase sample from separation vessel 110, and configured to draw a measured amount of fresh water from fresh water reservoir 135, using sensors (e.g., flow meters), so that the nondiluted aqueous liquid phase sample and the fresh water are mixed at a predetermined ratio (e.g., 10:1) to generate the diluted aqueous liquid phase sample. Mixing and generation of the diluted aqueous liquid phase sample may occur outside (e.g., at junction 132 of FIG. 1) and/or inside (e.g., analytical cell 150 of) water analysis unit 140. For example, at blocks 225 and 230, control unit 180 may be configured so that first, the measured amount of fresh water is flown into analytical cell 150 of the water analysis unit 140, and second, the nondiluted aqueous liquid phase sample is flown into analytical cell 150, so that the mixing and generation of the diluted aqueous liquid phase sample occurs inside water analysis unit 140.

Operations of blocks 225 and 230 is further illustrated by way of example, with reference to separation vessel 110 of FIG. 1. Since the discrete sample of multiphase fluid in separation vessel 110 has adequately separated into liquid phases including separate aqueous liquid phase 105 and separate nonporous liquid phase 104 (e.g., control unit determined that the corresponding predetermined period of time (e.g., 2 hours) has elapsed since end of the active mixing operation), control unit 180 at block 225 operates pump assembly 131 and sample control valve 129 to draw a measured amount of separated aqueous liquid phase 105 which has accumulated at the bottom of vessel 110 as the separated aqueous liquid phase sample, and control unit 180 at block 230 operates pump assembly 131 and fresh water control valve 134 to draw a measured amount of fresh water from reservoir 135, so that an aqueous liquid phase sample stream flowing from vessel 110 via couplings 130 and 136 combines and mixes with a fresh water stream flowing from reservoir 135 via couplings 133 and 136, to generate the diluted aqueous liquid phase sample 105A, as it enters analytical cell 150 of water analysis unit 140. At block 230, control unit 180 controls flow of the diluted aqueous liquid phase sample so that the diluted aqueous liquid phase sample 105A in analytical cell 150 comes in predetermined contact with (modified or unmodified) membrane-coated sensor tips 170A-170C of probes 160A-160C disposed inside analytical cell 150. That is, control unit 180 controls to fill analytical cell 150 with the diluted aqueous liquid phase sample so that, as shown in FIG. 1, the (modified or unmodified) membrane-coated sensor tips 170A-170C are completely immersed in and maintain predetermined contact with the diluted aqueous liquid phase sample 105A.

Method 200 then proceeds to block 235 where the diluted aqueous liquid phase sample 105A introduced in analytical cell 150 is analyzed with probes 160 to obtain diluted aqueous liquid phase sample data (e.g., set of measurement data corresponding to diluted aqueous liquid phase sample of block 230). At block 240, control unit 180 accounts for the dilution of the aqueous liquid phase sample of block 230 by performing predetermined processing on the diluted aqueous liquid phase sample data to obtain nondiluted aqueous liquid phase sample data (e.g., set of measurement data corresponding to nondiluted aqueous liquid phase sample of block 225).

Continuing with the above example of FIG. 1, control unit 180 at block 235 may transmit control signals to probes 160A-160C to cause probes 160A-160C to continuously measure and transmit sensor data to control unit 180. Control unit 180 may be configured to maintain the predetermined contact in analytical cell 150 of probes 160 with the sample until the continuously received sensor data from sensors 160A-160C stabilizes, thereby indicating that a steady reading has been obtained. The control unit 180 may be configured to record in memory the stabilized sensor data as diluted aqueous liquid phase sample data (e.g., set of measurement data corresponding to diluted aqueous liquid phase sample). Further, control unit 180 is configured to perform predetermined operations (e.g., account for the fresh water added to the aqueous liquid phase sample) on the diluted aqueous liquid phase sample data to obtain sensor data corresponding to the nondiluted aqueous liquid phase sample obtained from separation vessel 110 (e.g., set of measurement data corresponding to nondiluted aqueous liquid phase sample). For example, control unit 180 may control to allow 1:10 dilution (v/v) to take place, i.e. ten times dilution of the produced water sample by adding fresh water. Once the diluted aqueous liquid phase sample data corresponding to the 1:10 diluted produced water sample is obtained, control unit 180 multiplies the measured values by ten times of correct for the dilution effect, to obtain back calculated values as the nondiluted aqueous liquid phase sample data corresponding to the nondiluted produced water. Control unit 180 may store the nondiluted aqueous liquid phase sample data in memory, along with corresponding data regarding the multiphase fluid in separation vessel 110, and other corresponding data. Further, the (modified or unmodified) membrane-coated sensor tips 170A-170C ensure that accurate data is measured by probes 160 even if trace amounts of oil is present in the diluted aqueous liquid phase sample.

At block 245, control unit 180 may transmit the (nondiluted) aqueous liquid phase sample data obtained at block 240 to MPFM 190 to calibrate, optimize, or control MPFM 190 so that MPFM 190 can detect flow rates of oil and produced water passing therethrough more accurately. As a result of method 200, MPFM 190 is able to more accurately detect the constituent flow rates of various liquid phases (e.g., crude oil, produced water) of the multiphase fluid whose sample was analyzed at block 235 and that is being produced from a corresponding well or group of wells whose output is flowing through a flowpath of MPFM 190. Method 200 then proceeds to block 250 where control unit 180 operates control valve 192 and/or pump assembly (not shown in FIG. 1) to drain the diluted aqueous liquid phase sample from analytical cell 150 and into drain equipment 195. At block 255, control unit 180 may control pump assembly 131 and control valve 134 to flow fresh water from fresh water reservoir 135 into analytical cell 150 to rinse it and prepare the cell for a next diluted sample. For example, after draining the sample at block 250, control unit 180 may cause fresh water to fill analytical cell 150 and further drain the fresh water therefrom into drain equipment 195. This process may be performed one or more times, to prevent cross contamination between samples to be analyzed consecutively by same analytical cell 150. Next, at block 260, control unit 180 controls drain control valve 196 of separation vessel 110 to drain the demulsified multiphase fluid contained in separation vessel 110 to drain equipment 195.

Continuing with the above example of FIG. 1, control unit 180 at block 260 controls drain control valve 196 to be in an open position (and optionally, drive a pump assembly (not shown)) to drain the demulsified and separated multiphase fluid out of separation vessel 110 via drain coupling 197 to drain equipment 195. At block 260, control unit 180 may continue to drain demulsified and separated multiphase fluid out of separation vessel 110 until sensor data received from second level indicator 107 indicates that separation vessel 110 is empty. Control unit 180 at block 260 may also perform operations to rinse empty separation vessel 110 with fresh water from reservoir 135 prior to selectively filling separation vessel 110 with another discrete sample of multiphase fluid to prevent cross contamination between consecutive samples of multiphase fluid to be contained in separation vessel 110.

Method 200 next proceeds to block 265 where control unit 180 determines (e.g., based on sensor data associated with holding chamber 115) whether multiphase fluid whose sample needs to be analyzed by water analysis unit 140 is present in holding chamber 115. In response to determining that a multiphase fluid whose sample needs to be analyzed is present in holding chamber 115 (YES at block 265), method 200 proceeds to block 205, and the steps of method 200 are repeated to analyze the new discrete sample of multiphase fluid. On the other hand, in response to determining that a multiphase fluid whose sample needs to be analyzed is not present in holding chamber 115 (NO at block 265), method 200 waits until a new sample becomes available in holding chamber 115 for analysis.

In this manner, multiple samples are continuously analyzed by the system and method and corresponding measurement data recorded automatically. Further, the (modified or unmodified) membrane-coated sensor tips 170A-170C of probes 160A-160C ensure that the measurement operation can be repeatedly and accurately performed for the multiphase fluid samples for long periods of time, without requiring frequent cleaning of the electrodes.

Example

The following example is included to demonstrate embodiments of the disclosure, and should be considered nonlimiting. The example which follows represents techniques, systems, compositions, and apparatuses discovered to function well in the practice of the disclosure, and thus can be considered to constitute modes for its practice. However, changes can be made to the embodiment disclosed in the example without departing from the spirit and scope of the disclosure.

Example 1—Laboratory-scale experiment using a system for separating a multiphase fluid, and diluting and analyzing the aqueous liquid phase separated from the multiphase fluid.

A laboratory-scale experiment was carried out using a system for separating a multiphase fluid, and diluting and analyzing the aqueous liquid phase similar to the system and process shown in connection FIG. 1 and FIG. 2. Four multiphase samples having varying ratios of oil to produced water between 93/7 and 97/3 by volume were tested. The samples were taken from various gas-oil separation plants. The system included a separation vessel made of shatterproof glass. The system further included a water analysis unit including an analytical cell having ion-selective electrodes for measuring conductivity, chloride, and total dissolved solids (TDS).

Sensing areas of the ion-selective electrodes were coated with an ion-exchange membrane made with a sulfonated tetrafluoroethylene-based fluoropolymer-copolymer, available under the brand name Nafion™ 117. The Nafion™ 117 ion-exchange membrane used for coating the sensing area surfaces of the ion-selective electrodes for measuring conductivity and TDS was subject to treatment in which the Nafion™ 117 ion-exchange membrane was boiled with pure phosphoric acid to change the molecular structure or arrangement of the ion-exchange membrane and thereby enable the measurement operation to remain accurate for longer periods of time even in the presence of small amounts of oil in the produced water sample. The Nafion™ 117 ion-exchange membrane used for coating the sensing area of the ion-selective electrodes for measuring chloride content was not subject to the treatment of boiling with pure phosphoric acid. That is, the sensing area of the ion-selective electrode for measuring chloride content was coated with the Nafion™ 117 ion-exchange membrane whose molecular structure or arrangement was left unchanged to enable unhindered measurement of sodium in the produced water.

The system was configured to automatically fill the separation vessel with a multiphase fluid from a gas-oil separation plant, introduce a demulsifier, operate a mixer to actively mix the demulsifier and the multiphase fluid, and allow separation of the aqueous liquid phase and the nonpolar liquid phase to be carried out for a period of about 2 hours. The aqueous liquid phase and the nonpolar liquid phase separated after about 2 hours, with the aqueous liquid phase settling underneath the nonpolar liquid phase. A measured amount of the aqueous liquid phase was automatically drawn from the lower portion of the separation vessel, diluted with a measured amount of fresh water including deionized water from a fresh water reservoir, and sent to the water analysis unit. The dilution ratio between the fresh water and the aqueous liquid phase sample was 10:1 (v/v). The diluted sample was allowed to settle in the analytical cell for 10 minutes, so that readings from the three probes (ion-selective electrodes) were stable. Readings from the probes were sent to an analog-digital convertor, which produced digital data that was sent to a control unit. The water analysis unit was configured to carry out the analysis automatically. Approximate values of the same properties for the nondiluted aqueous liquid phase were calculated by accounting for the degree of dilution, and the calculated nondiluted aqueous liquid phase sample data was then recorded for each of the four multiphase fluid samples.

After the analysis and measurement, and recording of the measured data for each sample, the diluted sample in the water analysis unit and the multiphase fluid in the separation vessel were flushed and rinsed with deionized water, and the process was repeated with a subsequent discrete multiphase fluid sample. The calculated approximate values for each sample were compared to values for the same samples that were calculated using conventional lab-based techniques, to determine whether each of the sodium electrode, conductivity electrode, and TDS electrode were outputting values that were accurate. Results of the comparison are tabulated below in Table 1:

|                         |                   | Electrode Performance |                         |                  |
|-------------------------|-------------------|-----------------------|-------------------------|------------------|
| Multiphase fluid Sample | Oil/Water (v/v)   | Sodium Electrode      | Conductivity Electrode  | TDS Electrode    |
| 1                       | 3/97              | No Issues             | No Issues               | No Issues        |
| 2                       | 4/96              | No Issues             | No Issues               | No Issues        |

| Multiphase fluid Sample | Oil/Water (v/v) | Electrode Performance | | |
|---|---|---|---|---|
| | | Sodium Electrode | Conductivity Electrode | TDS Electrode |
| 3 | 5/95 | No Issues | Slow Response | Poor Response |
| 4 | 6/94 | Slow Response | Very Poor Response | No Response |

As can be seen from the above results, no issues were found with respect to the first two samples (Sample Nos. 1 and 2 in Table 1). Samples 3 and 4 generated results that were different from the conventional lab-based results, and therefore deemed inaccurate.

Figure 3:
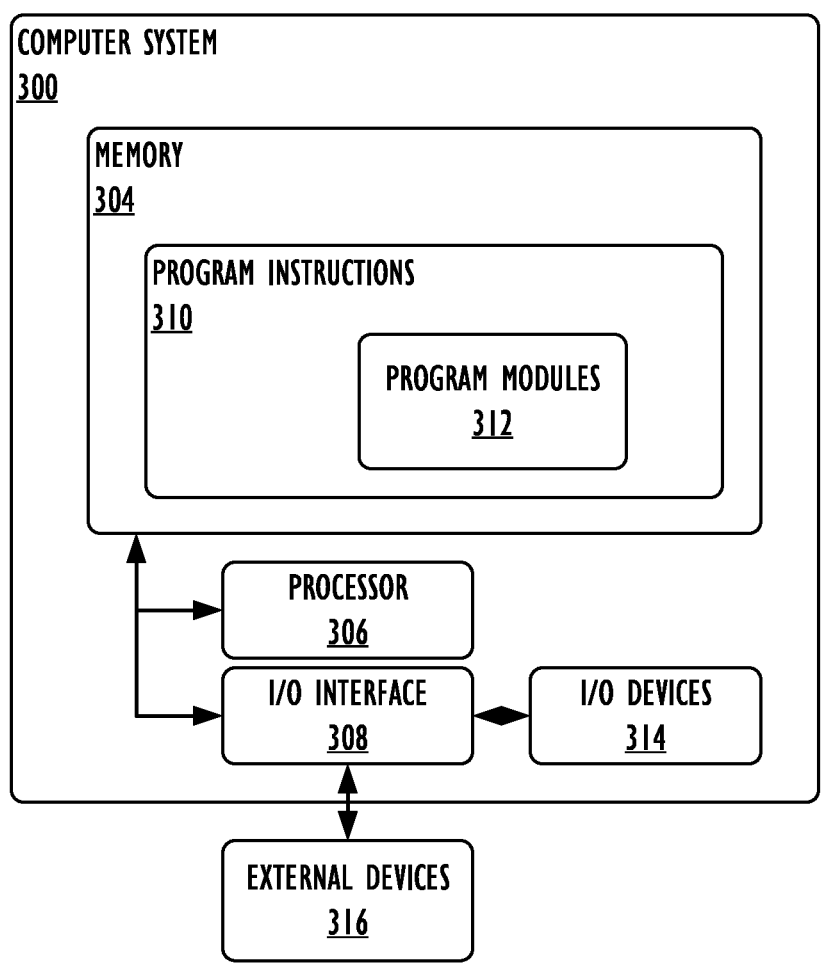
FIG. 3 is a functional block diagram of an exemplary computer system, in accordance with one or more embodiments.

FIG. 3 is a functional block diagram of an exemplary computer system (or "system") 300 in accordance with one or more embodiments. In some embodiments, system 300 is a PLC, system on a chip, ASIC, and the like. System 300 may include memory 304, processor 306 and input/output (I/O) interface 308. Memory 304 may include non-volatile memory (e.g., flash memory, solid state memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), or bulk storage memory (e.g., CD-ROM or DVD-ROM, hard drives). Memory 304 may include a non-transitory computer-readable storage medium (e.g., non-transitory program storage device) having program instructions 310 stored thereon. Program instructions 310 may include program modules 312 that are executable by a computer processor (e.g., processor 306) to cause the functional operations described herein, such as those described with regard to control unit 180, MPFM 190, or method 200.

Processor 306 may be any suitable processor capable of executing program instructions. Processor 306 may include a central processing unit (CPU) that carries out program instructions (e.g., the program instructions of the program modules 312) to perform the arithmetical, logical, or input/output operations described. Processor 306 may include one or more processors. I/O interface 308 may provide an interface for communication with one or more I/O devices 314, such as a joystick, a computer mouse, a keyboard, or a display screen (for example, an electronic display for displaying a graphical user interface (GUI)). I/O devices 314 may include one or more of the user input devices. I/O devices 314 may be connected to I/O interface 308 by way of a wired connection (e.g., an Industrial Ethernet connection) or a wireless connection (e.g., a Wi-Fi connection). I/O interface 308 may provide an interface for communication with one or more external devices 316. In some embodiments, I/O interface 308 includes one or both of an antenna and a transceiver. In some embodiments, external devices 316 include any of the electronic components communicatively coupled to control unit 180 and that are described above in connection with FIGS. 1 and 2.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (e.g., meaning having the potential to), rather than the mandatory sense (e.g., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (e.g., by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise.

Many other embodiments will be apparent to those of skill in the art upon reviewing the above description. The scope of the subject matter of the present disclosure therefore should be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A water analysis unit of a system for separating and analyzing multiphase fluids, the water analysis unit comprising:
    an analytical cell in fluid communication with a separation vessel, wherein the analytical cell has an inner chamber that is adapted to contain a diluted aqueous liquid phase sample for analysis; and
    a plurality of probes disposed in the inner chamber, each of the plurality of probes having a sensing area at a distal end, and being oriented in the inner chamber such that the sensing area is immersed in the diluted aqueous liquid phase sample when the diluted aqueous liquid phase sample is contained in the inner chamber, the plurality of probes including:
        a first probe whose sensing area surface is coated with a first ion-exchange membrane; and
        a second probe whose sensing area surface is coated with a second ion-exchange membrane, the second ion-exchange membrane being different from the first ion-exchange membrane.

2. The water analysis unit according to claim 1, wherein each of the first and second ion-exchange membranes is made of a sulfonated tetrafluoroethylene based fluoropolymer-copolymer.

3. The water analysis unit according to claim 1, wherein each of the plurality of probes has an oblong shape, and wherein the sensing area at the distal end of the probe is fully covered with the first or second ion-exchange membrane.

4. The water analysis unit according to claim 1, wherein a thickness of the first or second ion-exchange membrane is between 0.003 inches and 0.01 inches.

5. The water analysis unit according to claim 1, wherein the first ion-exchange membrane is a perfluorinated membrane having hydrophilic properties, and wherein the second ion-exchange membrane is an instance of the first ion-exchange membrane that has been modified by subjecting it to a predetermined treatment.

6. The water analysis unit according to claim 5, wherein the predetermined treatment includes a boiling treatment of boiling the instance of the first ion-exchange membrane with phosphoric acid to modify a molecular structure of a polar material of the instance of the first ion-exchange membrane.

7. The water analysis unit according to claim 6, wherein the first probe includes a first ion-selective electrode that is configured to measure a sodium or chloride concentration of the diluted aqueous liquid phase sample, and wherein the second probe includes a second ion-selective electrode that is configured to measure one or more properties of the diluted aqueous liquid phase sample, the one or more properties selected from a group including: a total dissolved solids (TDS), pH, conductivity, sulfate concentration, carbonate concentration, and nitrate concentration and any combination of the same.

8. The water analysis unit according to claim 7, wherein the plurality of probes further comprise a third probe that includes a third ion-selective electrode configured to measure another one or more properties of the diluted aqueous liquid phase sample, the other one or more properties selected from the group including: TDS, pH, conductivity, sulfate concentration, carbonate concentration, and nitrate concentration.

9. The water analysis unit according to claim 1, wherein the plurality of probes are proximally disposed adjacent to each other such that each probe is oriented in the inner chamber in a fixed position with the sensing area in a downward direction and such that there exists an acute angle measured from the probe to a horizontal plane that is substantially perpendicular to a direction of gravity.

10. The water analysis unit according to claim 9, wherein the acute angle is in the range of 30°-60°.

11. The water analysis unit according to claim 1, wherein the analytical cell has a conical shape where a first width of the inner chamber on a side of a sample inlet of the analytical cell is greater than a second width of the inner chamber on a side of a sample outlet of the analytical cell.

12. The water analysis unit according to claim 11, wherein the inner chamber of the analytical cell defines a space having a shape that funnels liquid toward the sample outlet.

13. The water analysis unit according to claim 1, wherein the separation vessel is external to the water analysis unit, wherein the analytical cell is in further fluid communication with an external fresh water reservoir, and wherein the diluted aqueous liquid phase sample adapted to be contained in the analytical cell includes an aqueous liquid phase sample from the external separation vessel and a measured amount of fresh water from the external fresh water reservoir.

14. The water analysis unit according to claim 13, further comprising one or more processors operatively coupled to the plurality of probes, the one or more processors configured to:

obtain a set of measurement data from the plurality of probes as diluted aqueous liquid phase sample data;

calculate nondiluted aqueous liquid phase sample data corresponding to the aqueous liquid phase sample from the external separation vessel, based on the diluted aqueous liquid phase sample data and based on the measured amount of fresh water in the diluted aqueous liquid phase sample; and transmit the nondiluted aqueous liquid phase sample data to an external multiphase flow meter.

15. A method for analyzing a diluted aqueous liquid phase sample, the method comprising:

introducing a diluted aqueous liquid phase sample into an analytical cell, the diluted aqueous liquid phase sample including an aqueous liquid phase sample separated from a multiphase fluid in a separation vessel, and a measured amount of fresh water from a fresh water reservoir;

analyzing the diluted aqueous liquid phase sample contained in the analytical cell with a plurality of probes disposed in an inner chamber of the analytical cell, each of the plurality of probes having a sensing area at a distal end, and being oriented in the inner chamber such that the sensing area is immersed in the diluted aqueous liquid phase sample contained in the analytical cell, wherein the plurality of probes include: a first probe whose sensing area surface is coated with a first ion-exchange membrane, and a second probe whose sensing area surface is coated with a second ion-exchange membrane, the second ion-exchange membrane being different from the first ion-exchange membrane;

obtaining a set of measurement data from the plurality of probes based on the analysis as diluted aqueous liquid phase sample data;

calculating nondiluted aqueous liquid phase sample data corresponding to the aqueous liquid phase sample separated from the multiphase fluid in the separation vessel, based on the diluted aqueous liquid phase sample data and based on the measured amount of fresh water in the diluted aqueous liquid phase sample; and transmitting the nondiluted aqueous liquid phase sample data to an external multiphase flow meter.

16. The method according to claim 15, wherein the first ion-exchange membrane is a perfluorinated membrane having hydrophilic properties, and wherein the second ion-exchange membrane is an instance of the first ion-exchange membrane that has been modified by subjecting it to a predetermined treatment, and wherein the predetermined treatment includes a boiling treatment of boiling the instance of the first ion-exchange membrane with phosphoric acid to modify a molecular structure of a polar material of the instance of the first ion-exchange membrane.

17. The method according to claim 16, wherein the first probe includes a first ion-selective electrode that is configured to measure a sodium or chloride concentration of the diluted aqueous liquid phase sample, and wherein the second probe includes a second ion-selective electrode that is configured to measure one or more properties of the diluted aqueous liquid phase sample, the one or more properties selected from a group including: a total dissolved solids (TDS), pH, conductivity, sulfate concentration, carbonate concentration, and nitrate concentration.

18. A system for separating and analyzing a discrete sample of multiphase fluid, the system comprising:

a separation vessel having a first inner chamber adapted to contain a discrete sample of multiphase fluid;

an analytical cell in fluid communication with the separation vessel, wherein the analytical cell has a second inner chamber is adapted to contain a diluted aqueous liquid phase sample for analysis; and a plurality of probes disposed in the second inner chamber, each of the plurality of probes having a sensing area at a distal end, and being oriented in the second inner chamber such that the sensing area is immersed in the diluted aqueous liquid phase sample when the diluted aqueous liquid phase sample is contained in the second inner chamber, the plurality of probes including:

a first probe whose sensing area surface is coated with a first ion-exchange membrane; and a second probe whose sensing area surface is coated with a second ion-exchange membrane, the second ion-exchange membrane being different from the first ion-exchange membrane.

19. The system according to claim 18, wherein the first ion-exchange membrane is a perfluorinated membrane having hydrophilic properties, and wherein the second ion-exchange membrane is an instance of the first ion-exchange membrane that has been modified by subjecting it to a predetermined treatment, and wherein the predetermined treatment includes a boiling treatment of boiling the instance of the first ion-exchange membrane with phosphoric acid to modify a molecular structure of a polar material of the instance of the first ion-exchange membrane.

20. The system according to claim 18, wherein the first probe includes a first ion-selective electrode that is configured to measure a sodium or chloride concentration of the diluted aqueous liquid phase sample, and the second probe includes a second ion-selective electrode that is configured to measure a total dissolved solids concentration of the diluted aqueous liquid phase sample, and wherein the plurality of probes further comprise a third probe that includes a third ion-selective electrode configured to measure a conductivity of the diluted aqueous liquid phase sample.

21. The system according to claim 18, further comprising one or more processors operatively coupled to the plurality of probes, the one or more processors being configured to:

introduce the discrete sample of multiphase fluid into the separation vessel via a multiphase fluid inlet of the separation vessel;

mix a predetermined amount and type of demulsifier obtained from a demulsifier source with the discrete sample of multiphase fluid in the separation vessel to cause the discrete sample to separate into liquid phases including an aqueous liquid phase and a nonpolar liquid phase;

draw from the separation vessel, a sample of the aqueous liquid phase in response to determining that the discrete sample has separated into the liquid phases including the aqueous liquid phase and the nonpolar liquid phase;

dilute the aqueous liquid phase sample drawn from the separation vessel with a predetermined amount of fresh water from a fresh water source to generate the diluted aqueous liquid phase sample;

introduce the diluted aqueous liquid phase sample into the analytical cell for analysis;

measure diluted aqueous liquid phase sample data by analyzing the diluted aqueous liquid phase sample with the plurality of probes disposed in the second inner chamber;

calculate the aqueous liquid phase sample data corresponding to the aqueous liquid phase sample based on the measured diluted aqueous liquid phase sample data and based on the predetermined amount of fresh water in the diluted aqueous liquid phase sample; and transmit the aqueous liquid phase sample data to an multiphase flow meter for calibration.

* * * * *